United States Patent [19]
Rollins et al.

[11] Patent Number: 6,040,428
[45] Date of Patent: Mar. 21, 2000

[54] PORCINE E-SELECTIN

[75] Inventors: Scott Rollins, Monroe; Russell P. Rother, Cheshire; Louis A. Matis, Southport; Mark J. Evans, Cheshire, all of Conn.

[73] Assignee: Alexion Pharmaceuticals, Inc., New Haven, Conn.

[21] Appl. No.: 09/276,197

[22] Filed: Mar. 25, 1999

Related U.S. Application Data

[62] Division of application No. 08/252,493, Jun. 1, 1994, Pat. No. 5,891,645.

[51] Int. Cl.⁷ .................................................. C07K 14/47
[52] U.S. Cl. ........................................... 530/350; 530/395
[58] Field of Search ................................................ 530/350

[56] References Cited

PUBLICATIONS

Nguyen et al., *Nature,* vol. 365, pp. 267–269, 1993.

*Primary Examiner*—Anthony C. Caputa
*Assistant Examiner*—Stephen Gucker

[57] ABSTRACT

A porcine E-selectin protein, its amino acid sequence, the sequence of a cDNA encoding the protein, antibodies reactive with the protein, and methods for the use of these molecules are disclosed. The molecules are used to diagnose the rejection of xenotransplanted pig organs, as well as to prevent and treat such transplant rejection.

3 Claims, 3 Drawing Sheets

```
SP    PO   MIASQFLSALPL
      HU   **********T*

LEC   PO   VLLLLRESGAWSYSTSTETMTFDDASAYCQQRYTHLVAIQNHAEIEYLNSTFNYSASYYWIGIRK
      HU   *-IK**NAY*E**************KE***ILSP*********

PO   INGTWTWIGTKKALTPEATNWAPGEPNNKQSNEDCVEIYIKRDKDSGKWNDERCSKKKLALCYT
      HU   V*NV*I*V**Q*PEK*********R******Q*P**M**D******

EGF   PO   AACTPTSCSGHGECIETINSSTCQCYPGFRGLQCEQ
      HU   **N******VNYK*D*SK***

CR1   PO   ABSENT
      HU   IVNCTALESPEHGSLVCSHPLGNFSYNSSCSISCDRGYLPSSMETMQCMSSGEWSAPIPACN

CR2   PO   VVECDALENPVNGVVTCPQ---SLPWNTTCAFECKEGFELIGPEHLQCTSSGSWDGKKPTCK
      HU   ****VTA**F*E*F*NPG*F******T*D*E*****M*AQS****NNE*****

CR3   PO   AVTCDTVGHPQNGDVSCNHSSIGEFAYKSTCHFTCAEGFGLQGPAQIECTAQGQWTQQAPVCK
      HU   ****RA*RQ****S*R*SPA*TF**S*N*E*M****V*T*****I*E

CR4   PO   ABSENT
      HU   AFQCTALSNPERGYMNCLPSASGSFRYGSSCEFSCEQGFVLKGSKRLQCGPTGEWDNEKPTCE

CR5   PO   AVKCPAVSQPKNGLVKFTHSPTGEFTYKSSCAFSCEEGFELRGSAQLACTSQGQWTQEVPSCQ
      HU   **R*DHPK*RCA*I***********YTE****E****

CR6   PO   VVQCSSLEVPREINMSCSGEPVFGAVCTFACPEGWMLNGSVALTCGATGHWSGILPTCE
      HU   KAGK***********TK*****T**A*R********L***

TM    PO   APAESKIPLAMGLAAGGVSFMTSASFLLWLLKRLRKR
      HU   TN*VAS*A*L*LL*L*P*****R*C***-

CYT   PO   AKKFVPSSSSECLQPNGSYQMPSDLI
      HU   ****ACQSSDKYIL
```

*FIG. 1*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1592 base pairs
      (B) TYPE: Nucleic Acid
      (C) STRANDEDNESS: Double
      (D) TOPOLOGY: Linear (ii) MOLECULE TYPE: cDNA to mRNA
      (A) DESCRIPTION: Porcine E-selectin (iii) HYPOTHETICAL: No (iv) ANTI-SENSE: No (xi) SEQUENCE DESCRIPTION: SEQ ID NO:1:

```
GAATTCGGCA CGAGGCAAGA GGCACGAAGC AAGCCAGAGC AACACAGGAN            50

GAATTTGACA CCAAGATAAA CACTTCACAA AACCAAAAGC ATTTCAAGTC           100

TCATCTTAGG ATCAAAAGAA CTCTTGAAGT C ATG ATT GCT TCA CAG           146
                                 Met Ile Ala Ser Gln
                                 -20
```

-continued

| | |
|---|---|
| TTT CTC TCT GCT CTC CCT TTG GTG CTT CTC CTG CTT AGA GAA<br>Phe Leu Ser Ala Leu Pro Leu Val Leu Leu Leu Leu Arg Glu<br>        -15              -10                   -5 | 188 |
| AGT GGA GCC TGG TCT TAC AGC GCC TCT ACA GAA ACC ATG ACT<br>Ser Gly Ala Trp Ser Tyr Ser Ala Ser Thr Glu Thr Met Thr<br>         1                  5                    10 | 230 |
| TTT GAT GAT GCC AGT GCT TAT TGC CAG CAG AGG TAC ACA CAT<br>Phe Asp Asp Ala Ser Ala Tyr Cys Gln Gln Arg Tyr Thr His<br>           15                   20                25 | 272 |
| CTG GTC GCA ATT CAA AAC CAT GCA GAG ATT GAA TAC CTG AAC<br>Leu Val Ala Ile Gln Asn His Ala Glu Ile Glu Tyr Leu Asn<br>           30                   35 | 314 |
| TCC ACG TTC AAC TAT TCA GCA AGT TAC TAC TGG ATT GGA ATC<br>Ser Thr Phe Asn Tyr Ser Ala Ser Tyr Tyr Trp Ile Gly Ile<br>40                     45                   50 | 356 |
| AGG AAG ATC AAT GGT ACA TGG ACA TGG ATA GGG ACC AAG AAG<br>Arg Lys Ile Asn Gly Thr Trp Thr Trp Ile Gly Thr Lys Lys<br>    55                   60                  65 | 398 |
| GCC TTG ACC CCA GAG GCC ACC AAC TGG GCT CCA GGT GAA CCA<br>Ala Leu Thr Pro Glu Ala Thr Asn Trp Ala Pro Gly Glu Pro<br>           70                   75                80 | 440 |
| AAT AAT AAG CAA AGC AAT GAG GAC TGT GTA GAG ATC TAC ATC<br>Asn Asn Lys Gln Ser Asn Glu Asp Cys Val Glu Ile Tyr Ile<br>           85                   90                95 | 482 |
| AAG AGA GAC AAG GAC TCG GGC AAG TGG AAT GAT GAG AGA TGC<br>Lys Arg Asp Lys Asp Ser Gly Lys Trp Asn Asp Glu Arg Cys<br>              100                   105 | 524 |
| AGC AAA AAG AAG CTC GCC TTG TGC TAC ACA GCT GCC TGT ACC<br>Ser Lys Lys Lys Leu Ala Leu Cys Tyr Thr Ala Ala Cys Thr<br>110                   115                  120 | 566 |
| CCT ACA TCC TGC AGC GGC CAT GGT GAA TGC ATA GAG ACC ATC<br>Pro Thr Ser Cys Ser Gly His Gly Glu Cys Ile Glu Thr Ile<br>           125                   130             135 | 608 |
| AAT AGC TCT ACT TGC CAG TGC TAC CCC GGC TTC CGA GGC CTC<br>Asn Ser Ser Thr Cys Gln Cys Tyr Pro Gly Phe Arg Gly Leu<br>           140                   145             150 | 650 |
| CAG TGT GAG CAA GTG GTT GAG TGT GAT GCT TTG GAA AAT CCT<br>Gln Cys Glu Gln Val Val Glu Cys Asp Ala Leu Glu Asn Pro<br>              155                   160             165 | 692 |
| GTC AAC GGA GTC GTG ACA TGT CCC CAA AGC CTC CCA TGG AAC<br>Val Asn Gly Val Val Thr Cys Pro Gln Ser Leu Pro Trp Asn<br>              170                   175 | 734 |
| ACA ACC TGT GCA TTT GAG TGT AAG GAA GGA TTT GAA CTC ATT<br>Thr Thr Cys Ala Phe Glu Cys Lys Glu Gly Phe Glu Leu Ile<br>180                   185                  190 | 776 |
| GGA CCT GAG CAC CTG CAA TGT ACC TCA TCT GGG AGC TGG GAC<br>Gly Pro Glu His Leu Gln Cys Thr Ser Ser Gly Ser Trp Asp<br>           195                   200             205 | 818 |
| GGC AAG AAG CCA ACG TGT AAA GCT GTG ACA TGT GAC ACC GTC<br>Gly Lys Lys Pro Thr Cys Lys Ala Val Thr Cys Asp Thr Val<br>           210                   215             220 | 860 |
| GGC CAT CCT CAG AAT GGT GAT GTG AGT TGT AAC CAC TCC TCT<br>Gly His Pro Gln Asn Gly Asp Val Ser Cys Asn His Ser Ser<br>           225                   230             235 | 902 |
| ATT GGA GAG TTT GCC TAC AAG TCA ACC TGC CAC TTC ACC TGT<br>Ile Gly Glu Phe Ala Tyr Lys Ser Thr Cys His Phe Thr Cys<br>              240                   245 | 944 |

```
GCA GAA GGC TTC GGG CTG CAG GGG CCA GCC CAG ATT GAA TGC        986
Ala Glu Gly Phe Gly Leu Gln Gly Pro Ala Gln Ile Glu Cys
250                 255                 260

ACT GCC CAG GGG CAA TGG ACC CAG CAA GCC CCA GTT TGT AAA        1028
Thr Ala Gln Gly Gln Trp Thr Gln Gln Ala Pro Val Cys Lys
    265                 270                 275

GCT GTG AAA TGT CCT GCT GTC TCC CAG CCC AAG AAT GGC TTG        1070
Ala Val Lys Cys Pro Ala Val Ser Gln Pro Lys Asn Gly Leu
            280                 285                 290

GTG AAG TTT ACC CAT TCC CCG ACT GGA GAG TTT ACC TAC AAG        1112
Val Lys Phe Thr His Ser Pro Thr Gly Glu Phe Thr Tyr Lys
                295                 300                 305

TCC TCC TGT GCC TTC AGC TGT GAG GAA GGC TTT GAA TTA CGT        1154
Ser Ser Cys Ala Phe Ser Cys Glu Glu Gly Phe Glu Leu Arg
                    310                 315

GGA TCA GCT CAA CTT GCA TGC ACA TCT CAA GGA CAA TGG ACA        1196
Gly Ser Ala Gln Leu Ala Cys Thr Ser Gln Gly Gln Trp Thr
320                 325                 330

CAG GAG GTT CCC TCC TGC CAA GTG GTA CAG TGT TCA AGT TTG        1238
Gln Glu Val Pro Ser Cys Gln Val Val Gln Cys Ser Ser Leu
    335                 340                 345

GAG GTT CCC AGA GAG ATC AAC ATG AGC TGC AGT GGG GAG CCC        1280
Glu Val Pro Arg Glu Ile Asn Met Ser Cys Ser Gly Glu Pro
            350                 355                 360

GTG TTT GGT GCT GTG TGT ACA TTT GCC TGT CCT GAA GGA TGG        1322
Val Phe Gly Ala Val Cys Thr Phe Ala Cys Pro Glu Gly Trp
                365                 370                 375

ATG CTC AAT GGC TCT GTA GCT CTG ACG TGT GGT GCC ACA GGA        1364
Met Leu Asn Gly Ser Val Ala Leu Thr Cys Gly Ala Thr Gly
                    380                 385

CAC TGG TCT GGG ATG CTG CCT ACT TGT GAA GCT CCT GCT GAG        1406
His Trp Ser Gly Met Leu Pro Thr Cys Glu Ala Pro Ala Glu
390                 395                 400

TCC AAA ATT CCC TTG GCA ATG GGA CTT GCT GCT GGT GGA GTC        1448
Ser Lys Ile Pro Leu Ala Met Gly Leu Ala Ala Gly Gly Val
    405                 410                 415

TCC TTC ATG ACA TCA GCA TCA TTT CTC CTC TGG CTC CTG AAA        1490
Ser Phe Met Thr Ser Ala Ser Phe Leu Leu Trp Leu Leu Lys
            420                 425                 430

CGC CTT CGG AAG AGA GCA AAA AAA TTT GTT CCT TCC AGC AGC        1532
Arg Leu Arg Lys Arg Ala Lys Lys Phe Val Pro Ser Ser Ser
                435                 440                 445

TCC GAA TGC CTT CAA CCC AAT GGA TCC TAC CAA ATG CCT TCT        1574
Ser Glu Cys Leu Gln Pro Asn Gly Ser Tyr Gln Met Pro Ser
                    450                 455

GAC TTA ATT TAAGTCCAA                                          1592
Asp Leu Ile
460

(2) INFORMATION FOR SEQ ID NO:2:

(i) SEQUENCE CHARACTERISTICS:
        (A) LENGTH: 23 bases
        (B) TYPE: Nucleic Acid
        (C) STRANDEDNESS: Single
        (D) TOPOLOGY: Linear (ii) MOLECULE TYPE: Other nucleic acid
        (A) DESCRIPTION: Oligonucleotide primer
```

(iii) HYPOTHETICAL: No (iv) ANTI-SENSE: No (xi) SEQUENCE DESCRIPTION: SEQ ID NO:2:

TAYTACTGGA TWGGRATCMG RAA                                              23

(2) INFORMATION FOR SEQ ID NO:3:

(i) SEQUENCE CHARACTERISTICS:
            (A) LENGTH: 29 bases
            (B) TYPE: Nucleic Acid
            (C) STRANDEDNESS: Single
            (D) TOPOLOGY: Linear (ii) MOLECULE TYPE: Other nucleic acid
            (A) DESCRIPTION: Oligonucleotide primer (iii) HYPOTHETICAL: No (iv) ANTI-SENSE: Yes (xi) SEQUENCE DESCRIPTION: SEQ ID NO:3:

CTCTTGATRT AKATCTCCAC RCAGTCCTC                                        29

(2) INFORMATION FOR SEQ ID NO:4:

(i) SEQUENCE CHARACTERISTICS:
            (A) LENGTH: 4059 base pairs
            (B) TYPE: Nucleic Acid
            (C) STRANDEDNESS: Double
            (D) TOPOLOGY: Circular (ii) MOLECULE TYPE: Other nucleic acid
            (A) DESCRIPTION: Apex-1 Eukaryotic
                Expression Vector (xi) SEQUENCE DESCRIPTION: SEQ ID NO:4:

ACGCGTTGAC ATTGATTATT GACTAGTTAT TAATAGTAAT CAATTACGGG                 50

GTCATTAGTT CATAGCCCAT ATATGGAGTT CCGCGTTACA TAACTTACGG                 100

TAAATGGCCC CGCCTGGCTG ACCGCCCAAC GACCCCCGCC CATTGACGTC                 150

AATAATGACG TATGTTCCCA TAGTAACGCC AATAGGGACT TTCCATTGAC                 200

GTCAATGGGT GGACTATTTA CGGTAAACTG CCCACTTGGC AGTACATCAA                 250

GTGTATCATA TGCCAAGTAC GCCCCCTATT GACGTCAATG ACGGTAAATG                 300

GCCCGCCTGG CATTATGCCC AGTACATGAC CTTATGGGAC TTTCCTACTT                 350

GGCAGTACAT CTACGTATTA GTCATCGCTA TTACCATGGT GATGCGGTTT                 400

TGGCAGTACA TCAATGGGCG TGGATAGCGG TTTGACTCAC GGGGATTTCC                 450

AAGTCTCCAC CCCATTGACG TCAATGGGAG TTTGTTTTGG CACCAAAATC                 500

AACGGGACTT TCCAAAATGT CGTAACAACT CCGCCCCATT GACGCAAATG                 550

GGCGGTAGGC GTGTACGGTG GGAGGTCTAT ATAAGCAGAG CTCGTTTAGT                 600

GAACCGTCAG AATTCTGTTG GCTCGCGGT TGATTACAAA CTCTTCGCGG                  650

TCTTTCCAGT ACTCTTGGAT CGGAAACCCG TCGGCCTCCG AACGGTACTC                 700

CGCCACCGAG GGACCTGAGC GAGTCCGCAT CGACCGGATC GGAAAACCTC                 750

TCGACTGTTG GGGTGAGTAC TCCCTCTCAA AAGCGGGCAT GACTTCTGCG                 800

CTAAGATTGT CAGTTTCCAA AAACGAGGAG GATTTGATAT TCACCTGGCC                 850

```
CGCGGTGATG CCTTTGAGGG TGGCCGCGTC CATCTGGTCA GAAAAGACAA      900

TCTTTTTGTT GTCAAGCTTG AGGTGTGGCA GGCTTGAGAT CTGGCCATAC      950

ACTTGAGTGA CAATGACATC CACTTTGCCT TTCTCTCCAC AGGTGTCCAC     1000

TCCCAGGTCC AACTGCAGGT CGACCGGCTT GGTACCGAGC TCGGATCCAC     1050

TAGTAACGGC CGCCAGTGTG CTGGAATTCT GCAGATATCC ATCACACTGG     1100

CGGCCGCTCG AGCATGCATC TAGAACTTGT TTATTGCAGC TTATAATGGT     1150

TACAAATAAA GCAATAGCAT CACAAATTTC ACAAATAAAG CATTTTTTTC     1200

ACTGCATTCT AGTTGTGGTT TGTCCAAACT CATCAATGTA TCTTATCATG     1250

TCTGGATCGA TCCCGCCATG GTATCAACGC CATATTTCTA TTTACAGTAG     1300

GGACCTCTTC GTTGTGTAGG TACCGCTGTA TTCCTAGGGA AATAGTAGAG     1350

GCACCTTGAA CTGTCTGCAT CAGCCATATA GCCCCCGCTG TTCGACTTAC     1400

AAACACAGGC ACAGTACTGA CAAACCCATA CACCTCCTCT GAAATACCCA     1450

TAGTTGCTAG GGCTGTCTCC GAACTCATTA CACCCTCCAA AGTCAGAGCT     1500

GTAATTTCGC CATCAAGGGC AGCGAGGGCT TCTCCAGATA AAATAGCTTC     1550

TGCCGAGAGT CCCGTAAGGG TAGACACTTC AGCTAATCCC TCGATGAGGT     1600

CTACTAGAAT AGTCAGTGCG GCTCCCATTT TGAAAATTCA CTTACTTGAT     1650

CAGCTTCAGA AGATGGCGGA GGGCCTCCAA CACAGTAATT TTCCTCCCGA     1700

CTCTTAAAAT AGAAAATGTC AAGTCAGTTA AGCAGGAAGT GGACTAACTG     1750

ACGCAGCTGG CCGTGCGACA TCCTCTTTTA ATTAGTTGCT AGGCAACGCC     1800

CTCCAGAGGG CGTGTGGTTT TGCAAGAGGA AGCAAAAGCC TCTCCACCCA     1850

GGCCTAGAAT GTTTCCACCC AATCATTACT ATGACAACAG CTGTTTTTTT     1900

TAGTATTAAG CAGAGGCCGG GGACCCCTGG GCCCGCTTAC TCTGGAGAAA     1950

AAGAAGAGAG GCATTGTAGA GGCTTCCAGA GGCAACTTGT CAAAACAGGA     2000

CTGCTTCTAT TTCTGTCACA CTGTCTGGCC CTGTCACAAG GTCCAGCACC     2050

TCCATACCCC CTTTAATAAG CAGTTTGGGA ACGGGTGCGG GTCTTACTCC     2100

GCCCATCCCG CCCCTAACTC CGCCCAGTTC CGCCCATTCT CCGCCCCATG     2150

GCTGACTAAT TTTTTTTATT TATGCAGAGG CCGAGGCCGC CTCGGCCTCT     2200

GAGCTATTCC AGAAGTAGTG AGGAGGCTTT TTTGGAGGCC TAGGCTTTTG     2250

CAAAAAGGAG CTCCCAGCAA AAGGCCAGGA ACCGTAAAAA GGCCGCGTTG     2300

CTGGCGTTTT TCCATAGGCT CCGCCCCCCT GACGAGCATC ACAAAAATCG     2350

ACGCTCAAGT CAGAGGTGGC GAAACCCGAC AGGACTATAA AGATACCAGG     2400

CGTTTCCCCC TGGAAGCTCC CTCGTGCGCT CTCCTGTTCC GACCCTGCCG     2450

CTTACCGGAT ACCTGTCCGC CTTTCTCCCT TCGGGAAGCG TGGCGCTTTC     2500

TCAATGCTCA CGCTGTAGGT ATCTCAGTTC GGTGTAGGTC GTTCGCTCCA     2550

AGCTGGGCTG TGTGCACGAA CCCCCCGTTC AGCCCGACCC TGCGCCTTA     2600

TCCGGTAACT ATCGTCTTGA GTCCAACCCG GTAAGACACG ACTTATCGCC     2650

ACTGGCAGCA GCCACTGGTA ACAGGATTAG CAGAGCGAGG TATGTAGGCG     2700

GTGCTACAGA GTTCTTGAAG TGGTGGCCTA ACTACGGCTA CACTAGAAGG     2750

ACAGTATTTG GTATCTGCGC TCTGCTGAAG CCAGTTACCT TCGGAAAAAG     2800
```

```
AGTTGGTAGC TCTTGATCCG GCAAACAAAC CACCGCTGGT AGCGGTGGTT        2850

TTTTTGTTTG CAAGCAGCAG ATTACGCGCA GAAAAAAGG ATCTCAAGAA         2900

GATCCTTTGA TCTTTTCTAC GGGGTCTGAC GCTCAGTGGA ACGAAAACTC        2950

ACGTTAAGGG ATTTTGGTCA TGAGATTATC AAAAAGGATC TTCACCTAGA        3000

TCCTTTTAAA TTAAAAATGA AGTTTTAAAT CAATCTAAAG TATATATGAG        3050

TAAACTTGGT CTGACAGTTA CCAATGCTTA ATCAGTGAGG CACCTATCTC        3100

AGCGATCTGT CTATTTCGTT CATCCATAGT TGCCTGACTC CCCGTCGTGT        3150

AGATAACTAC GATACGGGAG GGCTTACCAT CTGGCCCCAG TGCTGCAATG        3200

ATACCGCGAG ACCCACGCTC ACCGGCTCCA GATTTATCAG CAATAAACCA        3250

GCCAGCCGGA AGGGCCGAGC GCAGAAGTGG TCCTGCAACT TTATCCGCCT        3300

CCATCCAGTC TATTAATTGT TGCCGGGAAG CTAGAGTAAG TAGTTCGCCA        3350

GTTAATAGTT TGCGCAACGT TGTTGCCATT GCTACAGGCA TCGTGGTGTC        3400

ACGCTCGTCG TTTGGTATGG CTTCATTCAG CTCCGGTTCC CAACGATCAA        3450

GGCGAGTTAC ATGATCCCCC ATGTTGTGCA AAAAAGCGGT TAGCTCCTTC        3500

GGTCCTCCGA TCGTTGTCAG AAGTAAGTTG GCCGCAGTGT TATCACTCAT        3550

GGTTATGGCA GCACTGCATA ATTCTCTTAC TGTCATGCCA TCCGTAAGAT        3600

GCTTTTCTGT GACTGGTGAG TACTCAACCA AGTCATTCTG AGAATAGTGT        3650

ATGCGGCGAC CGAGTTGCTC TTGCCCGGCG TCAATACGGG ATAATACCGC        3700

GCCACATAGC AGAACTTTAA AAGTGCTCAT CATTGGAAAA CGTTCTTCGG        3750

GGCGAAAACT CTCAAGGATC TTACCGCTGT TGAGATCCAG TTCGATGTAA        3800

CCCACTCGTG CACCCAACTG ATCTTCAGCA TCTTTTACTT TCACCAGCGT        3850

TTCTGGGTGA GCAAAAACAG GAAGGCAAAA TGCCGCAAAA AAGGGAATAA        3900

GGGCGACACG GAAATGTTGA ATACTCATAC TCTTCCTTTT TCAATATTAT        3950

TGAAGCATTT ATCAGGGTTA TTGTCTCATG AGCGGATACA TATTTGAATG        4000

TATTTAGAAA AATAAACAAA TAGGGGTTCC GCGCACATTT CCCCGAAAAG        4050

TGCCACCTG                                                     4059
```

(2) INFORMATION FOR SEQ ID NO:5:

(i) SEQUENCE CHARACTERISTICS:
        (A) LENGTH: 24 bases
        (B) TYPE: Nucleic Acid
        (C) STRANDEDNESS: Single
        (D) TOPOLOGY: Linear (ii) MOLECULE TYPE: Other nucleic acid
        (A) DESCRIPTION: Oligonucleotide primer (iii) HYPOTHETICAL: No (iv) ANTI-SENSE: No (xi) SEQUENCE DESCRIPTION: SEQ ID NO:5:

```
GGAGAGTTTG CCTACAAGTC AACC                                    24
```

(2) INFORMATION FOR SEQ ID NO:6:

(i) SEQUENCE CHARACTERISTICS:
        (A) LENGTH: 58 bases
        (B) TYPE: Nucleic Acid (C) STRANDEDNESS:  Single
            (D) TOPOLOGY:  Linear (ii) MOLECULE TYPE:  Other nucleic acid
            (A) DESCRIPTION:  Oligonucleotide primer (iii) HYPOTHETICAL:  No (iv) ANTI-SENSE:  Yes (xi) SEQUENCE DESCRIPTION:  SEQ ID NO:6:

CCCGAATTCC TGCAGGTTAA TGGTGATGGT GATGGTGTTT GGACTCAGCA            50

GGAGCTTC                                                          58

(2) INFORMATION FOR SEQ ID NO:7:

(i) SEQUENCE CHARACTERISTICS:
            (A) LENGTH:  275 base pairs
            (B) TYPE:  Nucleic Acid
            (C) STRANDEDNESS:  Double
            (D) TOPOLOGY:  Circular (ii) MOLECULE TYPE:  Other nucleic acid
            (A) DESCRIPTION:  pGEM-7Zf(+)446/483
                insert (iii) HYPOTHETICAL:  No (xi) SEQUENCE DESCRIPTION:  SEQ ID NO:7:

CATGCACATC TCAAGGACAA TGGACACAGG AGGTTCCCTC CTGCCAAGTG            50

GTACAGTGTT CAAGTTTGGA GGTTCCCAGA GAGATCAACA TGAGCTGCAG           100

TGGGGAGCCC GTGTTTGGTG CTGTGTGTAC ATTTGCCTGT CCTGAAGGAT           150

GGATGCTCAA TGGCTCTGTA GCTCTGACGT GTGGTGCCAC AGGACACTGG           200

TCTGGGATCC TGCCTACTTG TGAAGCTCCT GCTGAGTCCA AACACCATCA           250

CCATCACCAT TAACCTGCAG GAATT                                     275

(2) INFORMATION FOR SEQ ID NO:8:

(i) SEQUENCE CHARACTERISTICS:
            (A) LENGTH:  8932 base pairs
            (B) TYPE:  Nucleic Acid
            (C) STRANDEDNESS:  Double
            (D) TOPOLOGY:  Circular (ii) MOLECULE TYPE:  Other nucleic acid
            (A) DESCRIPTION:  Apex-3 Eukaryotic
                Expression Vector (xi) SEQUENCE DESCRIPTION:  SEQ ID NO:8:

GTGACCAATA CAAAACAAAA GCGCCCCTCG TACCAGCGAA GAAGGGGCAG            50

AGATGCCGTA GTCAGGTTTA GTTCGTCCGG CGGCGGGGGA TCTGTATGGT           100

GCACTCTCAG TACAATCTGC TCTGATGCCG CATAGTTAAG CCAGTATCTG           150

CTCCCTGCTT GTGTGTTGGA GGTCGCTGAG TAGTGCGCGA GCAAAATTTA           200

AGCTACAACA AGGCAAGGCT TGACCGACAA TTGCATGAAG AATCTGCTTA           250

GGGTTAGGCG TTTTGCGCTG CTTCGCGATG TACGGGCCAG ATATACGCGT           300

TGACATTGAT TATTGACTAG TTATTAATAG TAATCAATTA CGGGGTCATT           350

AGTTCATAGC CCATATATGG AGTTCCGCGT TACATAACTT ACGGTAAATG           400

GCCCGCCTGG CTGACCGCCC AACGACCCCC GCCCATTGAC GTCAATAATG           450

-continued

```
ACGTATGTTC CCATAGTAAC GCCAATAGGG ACTTTCCATT GACGTCAATG        500

GGTGGACTAT TTACGGTAAA CTGCCCACTT GGCAGTACAT CAAGTGTATC        550

ATATGCCAAG TACGCCCCCT ATTGACGTCA ATGACGGTAA ATGGCCCGCC        600

TGGCATTATG CCCAGTACAT GACCTTATGG GACTTTCCTA CTTGGCAGTA        650

CATCTACGTA TTAGTCATCG CTATTACCAT GGTGATGCGG TTTTGGCAGT        700

ACATCAATGG GCGTGGATAG CGGTTTGACT CACGGGGATT TCCAAGTCTC        750

CACCCCATTG ACGTCAATGG GAGTTTGTTT TGGCACCAAA ATCAACGGGA        800

CTTTCCAAAA TGTCGTAACA ACTCCGCCCC ATTGACGCAA ATGGGCGGTA        850

GGCGTGTACG GTGGGAGGTC TATATAAGCA GAGCTCGTTT AGTGAACCGT        900

CAGAATTCTG TTGGGCTCGC GGTTGATTAC AAACTCTTCG CGGTCTTTCC        950

AGTACTCTTG GATCGGAAAC CCGTCGGCCT CCGAACGGTA CTCCGCCACC       1000

GAGGGACCTG AGCGAGTCCG CATCGACCGG ATCGGAAAAC CTCTCGACTG       1050

TTGGGGTGAG TACTCCCTCT CAAAAGCGGG CATGACTTCT GCGCTAAGAT       1100

TGTCAGTTTC CAAAAACGAG GAGGATTTGA TATTCACCTG GCCCGCGGTG       1150

ATGCCTTTGA GGGTGGCCGC GTCCATCTGG TCAGAAAAGA CAATCTTTTT       1200

GTTGTCAAGC TTGAGGTGTG GCAGGCTTGA GATCTGGCCA TACACTTGAG       1250

TGACAATGAC ATCCACTTTG CCTTTCTCTC CACAGGTGTC CACTCCCAGG       1300

TCCAACTGCA GGTCGACCGG CTTGGTACCG AGCTCGGATC CTCTAGAGTC       1350

GACCTGCAGG CATGCAAGCT TGGCACTGGC CGTCGTTTTA CAACGTCGTG       1400

ACTGGGAAAA CCCTGGCGTT ACCCAACTTA ATCGCCTTGC AGCACATCCC       1450

CCTTTCGCCA GCTGGCGTAA TAGCGAAGAG GCCCGCACCG ATCCAGACAT       1500

GATAAGATAC ATTGATGAGT TTGGACAAAC CACAACTAGA ATGCAGTGAA       1550

AAAAATGCTT TATTTGTGAA ATTTGTGATG CTATTGCTTT ATTTGTAACC       1600

ATTATAAGCT GCAATAAACA AGTTAACAAC AACAATTGCA TTCATTTTAT       1650

GTTTCAGGTT CAGGGGGAGG TGTGGGAGGT TTTTTAAAGC AAGTAAAACC       1700

TCTACAAATG TGGTATGGCT GATTATGATC CCCAGGAAGC TCCTCTGTGT       1750

CCTCATAAAC CCTAACCTCC TCTACTTGAG AGGACATTCC AATCATAGGC       1800

TGCCCATCCA CCCTCTGTGT CCTCCTGTTA ATTAGGTCAC TTAACAAAAA       1850

GGAAATTGGG TAGGGGTTTT TCACAGACCG CTTTCTAAGG GTAATTTTAA       1900

AATATCTGGG AAGTCCCTTC CACTGCTGTG TTCCAGAAGT GTTGGTAAAC       1950

AGCCCACAAA TGTCAACAGC AGAAACATAC AAGCTGTCAG CTTTGCACAA       2000

GGGCCCAACA CCCTGCTCAT CAAGAAGCAC TGTGGTTGCT GTGTTAGTAA       2050

TGTGCAAAAC AGGAGGCACA TTTTCCCCAC CTGTGTAGGT TCCAAAATAT       2100

CTAGTGTTTT CATTTTTACT TGGATCAGGA ACCCAGCACT CCACTGGATA       2150

AGCATTATCC TTATCCAAAA CAGCCTTGTG GTCAGTGTTC ATCTGCTGAC       2200

TGTCAACTGT AGCATTTTTT GGGGTTACAG TTTGAGCAGG ATATTTGGTC       2250

CTGTAGTTTG CTAACACACC CTGCAGCTCC AAAGGTTCCC CACCAACAGC       2300

AAAAAAATGA AAATTTGACC CTTGAATGGG TTTTCCAGCA CCATTTTCAT       2350

GAGTTTTTTG TGTCCCTGAA TGCAAGTTTA ACATAGCAGT TACCCCAATA       2400
```

-continued

| | |
|---|---|
| ACCTCAGTTT TAACAGTAAC AGCTTCCCAC ATCAAAATAT TTCCACAGGT | 2450 |
| TAAGTCCTCA TTTAAATTAG GCAAAGGAAT TCCTCGACCT GCAGCCCAAG | 2500 |
| CTTGGCACTG GCGCCAGAAA TCCGCGCGGT GGTTTTTGGG GGTCGGGGGT | 2550 |
| GTTTGGCAGC CACAGACGCC CGGTGTTCGT GTCGCGCCAG TACATGCGGT | 2600 |
| CCATGCCCAG GCCATCCAAA AACCATGGGT CTGTCTGCTC AGTCCAGTCG | 2650 |
| TGGACCTGAC CCCACGCAAC GCCCAAAAGA ATAACCCCCA CGAACCATAA | 2700 |
| ACCATTCCCC ATGGGGACC CCGTCCCTAA CCCACGGGGC CGTGGCTAT | 2750 |
| GGCGGGCTTG CCGCCCCGAC GTTGGCTGCG AGCCCTGGGC CTTCACCCGA | 2800 |
| ACTTGGGGGT TGGGGTGGGG AAAAGGAAGA AACGCGGGCG TATTGGCCCC | 2850 |
| AATGGGGTCT CGGTGGGGTA TCGACAGAGT GCCAGCCCTG GGACCGAACC | 2900 |
| CCGCGTTTAT GAACAAACGA CCCAACACCC GTGCGTTTTA TTCTGTCTTT | 2950 |
| TTATTGCCGT CATAGCGCGG GTTCCTTCCG GTATTGTCTC CTTCCGTGTT | 3000 |
| TCAGTTAGCC TCCCCCATCT CCCGATCCCC ACGAGTGCTG GGGCGTCGGT | 3050 |
| TTCCACTATC GGCGAGTACT TCTACACAGC CATCGGTCCA GACGGCCGCG | 3100 |
| CTTCTGCGGG CGATTTGTGT ACGCCCGACA GTCCCGGCTC CGGATCGGAC | 3150 |
| GATTGCGTCG CATCGACCCT GCGCCCAAGC TGCATCATCG AAATTGCCGT | 3200 |
| CAACCAAGCT CTGATAGAGT TGGTCAAGAC CAATGCGGAG CATATACGCC | 3250 |
| CGGAGCCGCG GCGATCCTGC AAGCTCCGGA TGCCTCCGCT CGAAGTAGCG | 3300 |
| CGTCTGCTGC TCCATACAAG CCAACCACGG CCTCCAGAAG AAGATGTTGG | 3350 |
| CGACCTCGTA TTGGGAATCC CCGAACATCG CCTCGCTCCA GTCAATGACC | 3400 |
| GCTGTTATGC GGCCATTGTC CGTCAGGACA TTGTTGGAGC CGAAATCCGC | 3450 |
| GTGCACGAGG TGCCGGACTT CGGGGCAGTC CTCGGCCCAA AGCATCAGCT | 3500 |
| CATCGAGAGC CTGCGCGACG GACGCACTGA CGGTGTCGTC CATCACAGTT | 3550 |
| TGCCAGTGAT ACACATGGGG ATCAGCAATC GCGCATATGA AATCACGCCA | 3600 |
| TGTAGTGTAT TGACCGATTC CTTGCGGTCC GAATGGGCCG AACCCGCTCG | 3650 |
| TCTGGCTAAG ATCGGCCGCA GCGATCGCAT CCATGGCCTC CGCGACCGGC | 3700 |
| TGCAGAACAG CGGGCAGTTC GGTTTCAGGC AGGTCTTGCA ACGTGACACC | 3750 |
| CTGTGCACGG CGGGAGATGC AATAGGTCAG GCTCTCGCTG AATTCCCAA | 3800 |
| TGTCAAGCAC TTCCGGAATC GGGAGCGCGG CCGATGCAAA GTGCCGATAA | 3850 |
| ACATAACGAT CTTTGTAGAA ACCATCGGCG CAGCTATTTA CCCGCAGGAC | 3900 |
| ATATCCACGC CCTCCTACAT CGAAGCTGAA AGCACGAGAT TCTTCGCCCT | 3950 |
| CCGAGAGCTG CATCAGGTCG GAGACGCTGT CGAACTTTTC GATCAGAAAC | 4000 |
| TTCTCGACAG ACGTCGCGGT GAGTTCAGGC TTTTTCATAT CAAGCTGATC | 4050 |
| TTGCGGCACG CTGTTGACGC TGTTAAGCGG GTCGCTGCAG GGTCGCTCGG | 4100 |
| TGTTCGAGGC CACACGCGTC ACCTTAATAT GCGAAGTGGA CCTGGGACCG | 4150 |
| CGCCGCCCCG ACTGCATCTG CGTGTTCGAA TTCGCCAATG ACAAGACGCT | 4200 |
| GGGCGGGGTT TGTGTCATCA TAGAACTAAA GACATGCAAA TATATTTCTT | 4250 |
| CCGGGGACAC CGCCAGCAAA CGCGAGCAAC GGGCCACGGG GATGAAGCAG | 4300 |
| CCCGGCGGCA CCTCGCTAAC GGATTCACCA CTCCAAGAAT TGGAGCCAAT | 4350 |

```
CAATTCTTGC GGAGAACTGT GAATGCGCAA ACCAACCCTT GGCAGAACAT      4400

ATCCATCGCG TCCGCCATCT CCAGCAGCCG CACGCGGCGC ATCTCGGGGC      4450

CGACGCGCTG GGCTACGTCT TGCTGGCGTT CGCGACGCGA GGCTGGATGG      4500

CCTTCCCCAT TATGATTCTT CTCGCTTCCG GCGGCATCGG GATGCCCGCG      4550

TTGCAGGCCA TGCTGTCCAG GCAGGTAGAT GACGACCATC AGGGACAGCT      4600

TCAAGGATCG CTCGCGGCTC TTACCAGCGC CAGCAAAAGG CCAGGAACCG      4650

TAAAAAGGCC GCGTTGCTGG CGTTTTTCCA TAGGCTCCGC CCCCCTGACG      4700

AGCATCACAA AAATCGACGC TCAAGTCAGA GGTGGCGAAA CCCGACAGGA      4750

CTATAAAGAT ACCAGGCGTT TCCCCCTGGA AGCTCCCTCG TGCGCTCTCC      4800

TGTTCCGACC CTGCCGCTTA CCGGATACCT GTCCGCCTTT CTCCCTTCGG      4850

GAAGCGTGGC GCTTTCTCAT AGCTCACGCT GTAGGTATCT CAGTTCGGTG      4900

TAGGTCGTTC GCTCCAAGCT GGGCTGTGTG CACGAACCCC CCGTTCAGCC      4950

CGACCGCTGC GCCTTATCCG GTAACTATCG TCTTGAGTCC AACCCGGTAA      5000

GACACGACTT ATCGCCACTG GCAGCAGCCA CTGGTAACAG GATTAGCAGA      5050

GCGAGGTATG TAGGCGGTGC TACAGAGTTC TTGAAGTGGT GGCCTAACTA      5100

CGGCTACACT AGAAGGACAG TATTTGGTAT CTGCGCTCTG CTGAAGCCAG      5150

TTACCTTCGG AAAAAGAGTT GGTAGCTCTT GATCCGGCAA ACAAACCACC      5200

GCTGGTAGCG GTGGTTTTTT TGTTTGCAAG CAGCAGATTA CGCGCAGAAA      5250

AAAAGGATCT CAAGAAGATC CTTTGATCTT TTCTACGGGG TCTGACGCTC      5300

AGTGGAACGA AAACTCACGT TAAGGGATTT TGGTCATGAG ATTATCAAAA      5350

AGGATCTTCA CCTAGATCCT TTTAAATTAA AAATGAAGTT TTAAATCAAT      5400

CTAAAGTATA TATGAGTAAA CTTGGTCTGA CAGTTACCAA TGCTTAATCA      5450

GTGAGGCACC TATCTCAGCG ATCTGTCTAT TTCGTTCATC CATAGTTGCC      5500

TGACTCCCCG TCGTGTAGAT AACTACGATA CGGGAGGGCT TACCATCTGG      5550

CCCCAGTGCT GCAATGATAC CGCGAGACCC ACGCTCACCG GCTCCAGATT      5600

TATCAGCAAT AAACCAGCCA GCCGGAAGGG CCGAGCGCAG AAGTGGTCCT      5650

GCAACTTTAT CCGCCTCCAT CCAGTCTATT AATTGTTGCC GGGAAGCTAG      5700

AGTAAGTAGT TCGCCAGTTA ATAGTTTGCG CAACGTTGTT GCCATTGCTG      5750

CAGGCATCGT GGTGTCACGC TCGTCGTTTG GTATGGCTTC ATTCAGCTCC      5800

GGTTCCCAAC GATCAAGGCG AGTTACATGA TCCCCCATGT TGTGCAAAAA      5850

AGCGGTTAGC TCCTTCGGTC CTCCGATCGT TGTCAGAAGT AAGTTGGCCG      5900

CAGTGTTATC ACTCATGGTT ATGGCAGCAC TGCATAATTC TCTTACTGTC      5950

ATGCCATCCG TAAGATGCTT TTCTGTGACT GGTGAGTACT CAACCAAGTC      6000

ATTCTGAGAA TAGTGTATGC GGCGACCGAG TTGCTCTTGC CCGGCGTCAA      6050

CACGGGATAA TACCGCGCCA CATAGCAGAA CTTTAAAAGT GCTCATCATT      6100

GGAAAACGTT CTTCGGGGCG AAAACTCTCA AGGATCTTAC CGCTGTTGAG      6150

ATCCAGTTCG ATGTAACCCA CTCGTGCACC CAACTGATCT TCAGCATCTT      6200

TTACTTTCAC CAGCGTTTCT GGGTGAGCAA AAACAGGAAG GCAAAATGCC      6250

GCAAAAAAGG GAATAAGGGC GACACGGAAA TGTTGAATAC TCATACTCTT      6300
```

-continued

| | |
|---|---|
| CCTTTTTCAA TATTATTGAA GCATTTATCA GGGTTATTGT CTCATGAGCG | 6350 |
| GATACATATT TGAATGTATT TAGAAAAATA AACAAATAGG GGTTCCGCGC | 6400 |
| ACATTTCCCC GAAAAGTGCC ACCTGACGTC TAAGAAACCA TTATTATCAT | 6450 |
| GACATTAACC TATAAAAATA GGCGTATCAC GAGGCCCTTT CGTCTTCAAG | 6500 |
| AATTCTCATG TTTGACAGCT TATCGTAGAC ATCATGCGTG CTGTTGGTGT | 6550 |
| ATTTCTGGCC ATCTGTCTTG TCACCATTTT CGTCCTCCCA ACATGGGCA | 6600 |
| ATTGGGCATA CCCATGTTGT CACGTCACTC AGCTCCGCGC TCAACACCTT | 6650 |
| CTCGCGTTGG AAAACATTAG CGACATTTAC CTGGTGAGCA ATCAGACATG | 6700 |
| CGACGGCTTT AGCCTGGCCT CCTTAAATTC ACCTAAGAAT GGGAGCAACC | 6750 |
| AGCAGGAAAA GGACAAGCAG CGAAAATTCA CGCCCCCTTG GGAGGTGGCG | 6800 |
| GCATATGCAA AGGATAGCAC TCCCACTCTA CTACTGGGTA TCATATGCTG | 6850 |
| ACTGTATATG CATGAGGATA GCATATGCTA CCCGGATACA GATTAGGATA | 6900 |
| GCATATACTA CCCAGATATA GATTAGGATA GCATATGCTA CCCAGATATA | 6950 |
| GATTAGGATA GCCTATGCTA CCCAGATATA AATTAGGATA GCATATACTA | 7000 |
| CCCAGATATA GATTAGGATA GCATATGCTA CCCAGATATA GATTAGGATA | 7050 |
| GCCTATGCTA CCCAGATATA GATTAGGATA GCATATGCTA CCCAGATATA | 7100 |
| GATTAGGATA GCATATGCTA TCCAGATATT TGGGTAGTAT ATGCTACCCA | 7150 |
| GATATAAATT AGGATAGCAT ATACTACCCT AATCTCTATT AGGATAGCAT | 7200 |
| ATGCTACCCG GATACAGATT AGGATAGCAT ATACTACCCA GATATAGATT | 7250 |
| AGGATAGCAT ATGCTACCCA GATATAGATT AGGATAGCCT ATGCTACCCA | 7300 |
| GATATAAATT AGGATAGCAT ATACTACCCA GATATAGATT AGGATAGCAT | 7350 |
| ATGCTACCCA GATATAGATT AGGATAGCCT ATGCTACCCA GATATAGATT | 7400 |
| AGGATAGCAT ATGCTATCCA GATATTTGGG TAGTATATGC TACCCATGGC | 7450 |
| AACATTAGCC CACCGTGCTC TCAGCGACCT CGTGAATATG AGGACCAACA | 7500 |
| ACCCTGTGCT TGGCGCTCAG GCGCAAGTGT GTGTAATTTG TCCTCCAGAT | 7550 |
| CGCAGCAATC GCGCCCCTAT CTTGGCCCGC CCACCTACTT ATGCAGGTAT | 7600 |
| TCCCCGGGGT GCCATTAGTG GTTTTGTGGG CAAGTGGTTT GACCGCAGTG | 7650 |
| GTTAGCGGGG TTACAATCAG CCAAGTTATT ACACCCTTAT TTTACAGTCC | 7700 |
| AAAACCGCAG GGCGGCGTGT GGGGGCTGAC GCGTGCCCCC ACTCCACAAT | 7750 |
| TTCAAAAAAA AGAGTGGCCA CTTGTCTTTG TTTATGGGCC CCATTGGCGT | 7800 |
| GGAGCCCCGT TTAATTTTCG GGGGTGTTAG AGACAACCAG TGGAGTCCGC | 7850 |
| TGCTGTCGGC GTCCACTCTC TTTCCCCTTG TTACAAATAG AGTGTAACAA | 7900 |
| CATGGTTCAC CTGTCTTGGT CCCTGCCTGG GACACATCTT AATAACCCCA | 7950 |
| GTATCATATT GCACTAGGAT TATGTGTTGC CCATAGCCAT AAAATTCGTGT | 8000 |
| GAGATGGACA TCCAGTCTTT ACGGCTTGTC CCCACCCCAT GGATTTCTAT | 8050 |
| TGTTAAAGAT ATTCAGAATG TTTCATTCCT ACACTAGTAT TTATTGCCCA | 8100 |
| AGGGGTTTGT GAGGGTTATA TTGGTGTCAT AGCACAATGC CACCACTGAA | 8150 |
| CCCCCCGTCC AAATTTTATT CTGGGGGCGT CACCTGAAAC CTTGTTTTCG | 8200 |
| AGCACCTCAC ATACACCTTA CTGTTCACAA CTCAGCAGTT ATTCTATTAG | 8250 |

-continued

```
CTAAACGAAG GAGAATGAAG AAGCAGGCGA AGATTCAGGA GAGTTCACTG       8300

CCCGCTCCTT GATCTTCAGC CACTGCCCTT GTGACTAAAA TGGTTCACTA       8350

CCCTCGTGGA ATCCTGACCC CATGTAAATA AAACCGTGAC AGCTCATGGG       8400

GTGGGAGATA TCGCTGTTCC TTAGGACCCT TTTACTAACC CTAATTCGAT       8450

AGCATATGCT TCCCGTTGGG TAACATATGC TATTGAATTA GGGTTAGTCT       8500

GGATAGTATA TACTACTACC CGGGAAGCAT ATGCTACCCG TTTAGGGTTA       8550

ACAAGGGGC CTTATAAACA CTATTGCTAA TGCCCTCTTG AGGGTCCGCT        8600

TATCGGTAGC TACACAGGCC CCTCTGATTG ACGTTGGTGT AGCCTCCCGT       8650

AGTCTTCCTG GGCCCCTGGG AGGTACATGT CCCCCAGCAT TGGTGTAAGA       8700

GCTTCAGCCA AGAGTTACAC ATAAAGGCAA TGTTGTGTTG CAGTCCACAG       8750

ACTGCAAAGT CTGCTCCAGG ATGAAAGCCA CTCAGTGTTG GCAAATGTGC       8800

ACATCCATTT ATAAGGATGT CAACTACAGT CAGAGAACCC CTTTGTGTTT      8850

GGTCCCCCCC CGTGTCACAT GTGGAACAGG GCCCAGTTGG CAAGTTGTAC      8900

CAACCAACTG AAGGGATTAC ATGCACTGCC CC                         8932
```

(2) INFORMATION FOR SEQ ID NO:9:

(i) SEQUENCE CHARACTERISTICS:
        (A) LENGTH: 484 amino acids
        (B) TYPE: amino acid
        (C) STRANDEDNESS: Single
        (D) TOPOLOGY: Linear (ii) MOLECULE TYPE: cDNA to mRNA
        (A) DESCRIPTION: predicted amino acid sequence of
            Porcine E-selectin (xi) SEQUENCE DESCRIPTION: SEQ ID NO:9:

```
Met Ile Ala Ser Gln
    -20

Phe Leu Ser Ala Leu Pro Leu Val Leu Leu Leu Arg Glu
    -15             -10                  -5

Ser Gly Ala Trp Ser Tyr Ser Ala Ser Thr Glu Thr Met Thr
             1               5                   10

Phe Asp Asp Ala Ser Ala Tyr Cys Gln Gln Arg Tyr Thr His
                 15              20              25

Leu Val Ala Ile Gln Asn His Ala Glu Ile Glu Tyr Leu Asn
                     30              35

Ser Thr Phe Asn Tyr Ser Ala Ser Tyr Tyr Trp Ile Gly Ile
40              45                  50

Arg Lys Ile Asn Gly Thr Trp Thr Trp Ile Gly Thr Lys Lys
    55              60                  65

Ala Leu Thr Pro Glu Ala Thr Asn Trp Ala Pro Gly Glu Pro
        70              75              80

Asn Asn Lys Gln Ser Asn Glu Asp Cys Val Glu Ile Tyr Ile
            85              90              95

Lys Arg Asp Lys Asp Ser Gly Lys Trp Asn Asp Glu Arg Cys
                100             105

Ser Lys Lys Lys Leu Ala Leu Cys Tyr Thr Ala Ala Cys Thr
110             115                 120
```

-continued

```
Pro Thr Ser Cys Ser Gly His Gly Glu Cys Ile Glu Thr Ile
    125                 130                 135

Asn Ser Ser Thr Cys Gln Cys Tyr Pro Gly Phe Arg Gly Leu
        140                 145                 150

Gln Cys Glu Gln Val Val Glu Cys Asp Ala Leu Glu Asn Pro
            155                 160                 165

Val Asn Gly Val Val Thr Cys Pro Gln Ser Leu Pro Trp Asn
                170                 175

Thr Thr Cys Ala Phe Glu Cys Lys Glu Gly Phe Glu Leu Ile
180                 185                 190

Gly Pro Glu His Leu Gln Cys Thr Ser Ser Gly Ser Trp Asp
    195                 200                 205

Gly Lys Lys Pro Thr Cys Lys Ala Val Thr Cys Asp Thr Val
        210                 215                 220

Gly His Pro Gln Asn Gly Asp Val Ser Cys Asn His Ser Ser
            225                 230                 235

Ile Gly Glu Phe Ala Tyr Lys Ser Thr Cys His Phe Thr Cys
                240                 245

Ala Glu Gly Phe Gly Leu Gln Gly Pro Ala Gln Ile Glu Cys
250                 255                 260

Thr Ala Gln Gly Gln Trp Thr Gln Gln Ala Pro Val Cys Lys
    265                 270                 275

Ala Val Lys Cys Pro Ala Val Ser Gln Pro Lys Asn Gly Leu
        280                 285                 290

Val Lys Phe Thr His Ser Pro Thr Gly Glu Phe Thr Tyr Lys
            295                 300                 305

Ser Ser Cys Ala Phe Ser Cys Glu Glu Gly Phe Glu Leu Arg
                310                 315

Gly Ser Ala Gln Leu Ala Cys Thr Ser Gln Gly Gln Trp Thr
320                 325                 330

Gln Glu Val Pro Ser Cys Gln Val Val Gln Cys Ser Ser Leu
    335                 340                 345

Glu Val Pro Arg Glu Ile Asn Met Ser Cys Ser Gly Glu Pro
        350                 355                 360

Val Phe Gly Ala Val Cys Thr Phe Ala Cys Pro Glu Gly Trp
            365                 370                 375

Met Leu Asn Gly Ser Val Ala Leu Thr Cys Gly Ala Thr Gly
                380                 385

His Trp Ser Gly Met Leu Pro Thr Cys Glu Ala Pro Ala Glu
390                 395                 400

Ser Lys Ile Pro Leu Ala Met Gly Leu Ala Ala Gly Gly Val
    405                 410                 415

Ser Phe Met Thr Ser Ala Ser Phe Leu Leu Trp Leu Leu Lys
        420                 425                 430

Arg Leu Arg Lys Arg Ala Lys Lys Phe Val Pro Ser Ser Ser
            435                 440                 445

Ser Glu Cys Leu Gln Pro Asn Gly Ser Tyr Gln Met Pro Ser
                450                 455

Asp Leu Ile
460
```

PORCINE E-SELECTIN

This is a divisional of U.S. Ser. No. 08/252,493, filed Jun. 1, 1994, now U.S. Pat. No. 5,891,645.

FIELD OF THE INVENTION

This invention relates to xenotransplantation, and to the monitoring and modulation of the immune response to the xenotransplant. More specifically, the invention relates to the development of reagents and methods that will improve the ability to rapidly and specifically diagnose rejection of porcine xenotransplants by human patients. The invention also relates to compositions, including nucleic acid molecules, proteins (including antibodies), porcine cells, porcine tissues, and porcine organs, that will improve the outcome of the xenotransplantation of porcine cells, tissues, and organs into human recipients. To this end the invention provides a porcine E-selectin protein, its amino acid sequence, the sequence of a cDNA encoding the protein, antibodies reactive with the protein, and methods for the use of these molecules.

BACKGROUND OF THE INVENTION

Xenotransplant Rejection: There is an ongoing shortage of human organs for transplant. This shortage has resulted in a long felt need for organs, and has resulted in attempts to develop xenotransplantation technology.

The primary non-primate candidate donor species for clinical xenotransplantation (e.g., the transplantation of non-human organs into human recipients) has been the pig. Swine provide an abundant supply of organs that are similar in size, anatomy, and physiology to their human counterparts (Auchincloss, 1988; Najarian, 1992; and Somervile and d'Apice, 1993). Transplantation of porcine pancreatic islets and of a pig liver into human patients has been reported, (Makowka, et al., 1993; Satake, et al., 1993; Tibell, et al., 1993), but the outcomes of these transplants need to be improved. One improvement that is needed is better control (e.g., inhibition) of transplant rejection.

The rejection of transplanted organs may involve both an extremely rapid hyperacute rejection (HAR) phase and a slower cellular rejection phase. HAR of discordant (i.e., non-primate) xenotransplants is initiated by preformed "natural" antibodies that bind to donor organ endothelium and activate complement attack by the recipient immune system (Dalmasso, et al., 1992; and Tuso, et al., 1993).

Activation of complement leads to the generation of fluid phase (C3a, C5a) and membrane bound (C3b and C5b-9, i.e., C5b, C6, C7, C8, and C9) proteins with chemotactic, procoagulant, proinflammatory, adhesive, and cytolytic properties (Muler-Eberhard, 1988). Immunohistological analysis of hyperacutely rejected xenotransplants reveals antibody deposition, complement fixation, and vascular thrombosis as well as neutrophil infiltration (Zehr, et al., 1994; Auchincloss, 1988; Najarian, 1992; Somervile and d'Apice, 1993; and Mejia-Laguna, et al., 1972).

While HAR is a major impediment to the xenotransplantation of vascularized organs, some discordantly xenotransplanted tissues (e.g., porcine pancreatic islets) do not appear to be rejected by this mechanism. Methods for the control of the ITA are also available. These include interference with the antibody antigen reactions responsible for initiating the HAR response, either by removing the antibodies from the circulation or by interfering with the expression of the antigens (see U.S. Pat. No. 5,821,117, entitled "Xenotransplantation Therapies" and filed by Mauro S. Sandrin and Ian F. C. McKenzie on Mar. 15, 1994). Inhibition of complement attack on the xenotransplant may be accomplished by several means, including the use of complement inhibitors such as the 18kDa CSb-9 inhibitory protein and monoclonal antibodies against human C5b-9 proteins as taught in U.S. Pat. No. 5,135,916, issued Aug. 4, 1992.

In order to better understand the porcine xenograft rejection phenomenon, studies have been undertaken to investigate interactions between human white blood cells and porcine cells, particularly porcine aortic endothelial cells (PAEC). The role of neutrophils in the actual destruction of xenografts has not been well characterized, and the precise mechanism of complement independent neutrophil activation and adherence to xenograft endothelium has heretofore been unknown. Previous studies have shown that human complement component C3b (C3bi) deposited on PAEC mediates the binding of human neutrophils to the PAEC through interactions with the heterodimeric neutrophil cell surface receptor CD11b/CD18 (Vercellotti, et al., 1991). Furthermore, blocking HAR by inhibition or depletion of complement results in decreased neutrophil infiltration and increased xenograft survival, providing additional evidence for the role of complement in mediating human neutrophil binding to porcine endothelium.

However, a significant neutrophil infiltrate into PAEC monolayers has been observed even in the absence of complement activation (Leventhal, et al., 1993; and Pruitt, et al., 1991). The development of such infiltrates is believed to play an important role in xenograft rejection. Means and methods allowing the control or elimination of such interactions are thus needed in order to make the transplantation of porcine cells, tissues, or organs into human recipients more practicable.

E-selectin: E-selectin (also known as ELAM-1, CD62, and CD62E) is a cytokine inducible cell surface glycoprotein cell adhesion molecule that is found exclusively on endothelial cells. E-selectin mediates the adhesion of various leukocytes, including neutrophils, monocytes, eosinophils, natural killer (NK) cells and a subset of T cells, to activated endothelium (Bevilacqua, et al., 1989; Shimuzu, et al., 1991; Graber, et al., 1990; Carlos, et al., 1991; Hakkert, et al., 1991; and Picker, et al., 1991). The expression of E-selectin is induced on human endothelium in response to the cytokines IL-1 and TNF, as well as bacterial lipopolysaccharide (LPS), through transcriptional upregulation (Montgomery, et al., 1991).

Recently, the human leukocyte receptor for human E-selectin has been identified (Berg, et al., 1991 and Tyrrell, et al., 1991). This receptor contains sialic acid (sialyl Lewis x, and sialyl Lewis a) as a necessary component for interaction with the E-selectin protein.

Structurally, E-selectin belongs to a family of adhesion molecules termed "selections" that also includes P-selectin and L-selectin (see reviews in Lasky, 1992 and Bevilacqua and Nelson, 1993). These molecules are characterized by common structural features such as an amino-terminal lectin-like domain, an epidermal growth factor (EGF) domain, and a discrete number of complement repeat modules (approximately 60 amino acids each) similar to those found in certain complement binding proteins.

Clinically, increased E-selectin expression on endothelium is associated with a variety of acute and chronic leukocyte-mediated inflammatory reactions including allograft rejection (Allen, et al., 1993; Brockmeyer, et al., 1993; Ferran, et al., 1993; and Taylor, et al., 1992). Other leukocyte-mediated inflammatory reactions associated with increased E-selectin expression on endothelium include delayed type hypersensitivity, immune complex-mediated lung injury, psoriasis, contact dermatitis, inflammatory bowel disease, and arthritis (Bevilacqua, et al., 1989; Bevilacqua and Nelson, 1993; Cotran, et al., 1986; Koch, et al., 1991; Mulligan, et al., 1991; and Mulligan, et al., 1993).

Studies in which the expression of human E-selectin in cardiac and renal allografts undergoing acute cellular rejection was investigated have demonstrated that E-selectin expression is selectively upregulated in vascular endothelium of renal and cardiac tissue during acute rejection (Allen, et al., 1993; Brockmeyer, et al., 1993; Ferran, et al., 1993; and Taylor, et al., 1992). Additionally, increased E-selectin expression correlates with the early course of cellular rejection and corresponds to the migration of inflammatory cells into the graft tissue (Allen, et al., 1993; Brockmeyer, et al., 1993; Ferran, et al., 1993; and Taylor, et al., 1992). Taken together, these studies provide evidence that cytokine-induced expression of E-selectin by donor organ endothelium contributes to the binding and subsequent transmigration of inflammatory cells into the graft tissue and thereby plays an important role in acute cellular allograft rejection.

Endothelial cells have been shown to release a soluble form of E-selectin following in vitro activation (Pigott, et al., 1992; Newman, et al., 1993; and Leeuwenberg, et al., 1992). The demonstration of soluble E-selectin (sE-selectin) in the blood would therefore be taken as conclusive evidence of endothelial activation (Gearing and Newman, 1993). Table I shows the levels of sE-selectin found in healthy and sick patients in various studies, as reviewed in Gearing and Newman, 1993.

Elevated levels of sE-selectin have been found in diabetic patients independent of hypertension, nephropathy or renal failure, and whether or not they were insulin dependent (Gearing, et al., 1992 and Gearing and Newman, 1993). Similarly, sE-selectin was detected in patients with vasculidities including polyarteritis nodosum, giant cell arteritis, and scleroderma, with higher levels noted in lupus patients. Overall, however, there was no correlation with disease activity and only a weak correlation with the degree of organ involvement (Carson, et al., 1993). These studies suggest that the endothelium in these patients is activated, and that overt disease activity involves additional factors.

Soluble E-selectin levels have also shown marked elevations in sepsis, in one study a twenty-fold increase over the normal range (Newman, et al., 1993). In this and another study, the levels of sE-selectin appear to correlate with disease severity and/or outcome (Gearing and Newman, 1993). Higher levels or persistent elevation were associated with greater mortality and this is not unexpected in view of the widespread expression of E-selectin in most vessels in primates challenged with a lethal dose of live *E. Coli* (Redi, et al., 1991). Gram-negative as well as gram-positive infections seem to be associated with elevated levels. Patients with acute *Plasmodium falciparum* malaria have also shown elevated levels of sE-selectin (Hviid, et al., 1994, reviewed in Gearing and Newman, 1993).

There are two reports of sE-selectin in body fluids other than blood. One is from Dubois, et al., who detected sE-selectin in bronchioalveolar lavage (BAL) fluids from 16/50 patients with interstitial lung disease, but in only 2/16 control samples (Dubois, et al., unpublished, cited in Gearing and Newman, 1993). In the second, sE-selectin was recovered from BAL fluids of allergic subjects after segmental antigen challenge, but not saline challenge (Georas, et al., 1992).

Soluble E-selectin found in the blood is biologically active when measured by its ability to mediate adhesion of neutrophils to a surface. In the fluid-phase, recombinant soluble E-selectin can inhibit leukocyte adhesion (Lobb, et al., 1991). Furthermore, recombinant E-selectin, in either soluble or cell-surface bound forms, can activate the polymorphonuclear cell CD11b integrin receptor (Lo, et al., 1991 and Kuijpers, et al., 1991). The levels required for these effects are not found in the bloodstream, however such levels may be found at local sites of inflammation.

The mechanism of release of soluble E-selectin in vivo has not been established, but immunochemical evidence suggests a lost or defective cytoplasmic domain in the soluble E-selectin found in plasma. Unlike certain other cellular adhesion molecules, E-selectin does not appear to have an alternately spliced form lacking a transmembrane domain.

SUMMARY OF THE INVENTION

In view of the foregoing state of the art, it is an object of this invention to prevent and/or treat xenograft rejection of porcine organs, tissues, or cells through modulation of E-selectin mediated cell adhesion, and to provide a means for diagnostic monitoring of xenotransplant rejection by specific measurement of the amount of porcine E-selectin in the blood of the porcine xenotransplant recipient.

To achieve these and other goals, the invention provides:

1) An isolated porcine E-selectin protein including a core protein comprising the amino acid sequence set forth as amino acids 1 to 405 of SEQ ID NO:9. In addition to the core protein, such a porcine E-selectin protein may contain a membrane anchor sequence located carboxyl terminal to amino acid 405 of SEQ ID NO:9. Alternatively, the protein may be truncated. Examples of such truncated proteins include those that do not include the membrane anchor. For example, the protein may terminate at or near amino acid 405 of SEQ ID NO:9.

2) A porcine E-selectin gene, in the form of, for example, cDNA and genomic DNA molecules comprising porcine E-selectin coding sequences.

3) A method for producing porcine E-selectin by growing a recombinant host cell containing the gene of the invention (i.e., a nucleic acid molecule coding for porcine E-selectin). The host cell is grown so that it expresses the porcine E-selectin protein encoded by the gene of the invention and the expressed porcine E-selectin protein is then isolated.

4) Anti porcine E-selectin antibodies that bind to porcine E-selectin, but not to human E-selectin.

5) Therapeutic agents and methods for their use for the prevention and/or treatment of porcine xenograft rejection. These agents contain the E-selectin protein of paragraph 1, immediately above, and/or the anti-porcine E-selectin antibodies of paragraph 4, immediately above.

6) Agents for the diagnosis of porcine xenograft rejection based upon the anti-porcine E-selectin antibodies of paragraph 4, immediately above.

7) Methods for disrupting the porcine E-selectin gene in porcine cells, and the E-selectin negative porcine cells generated via such methods.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

BRIEF DESCRIPTION OF THE DRAWINGS

FIG. 1. Amino acid comparison and domain structure comparison of porcine and human E-selectin: The porcine (PO) E-selectin amino acid sequence was aligned to the sequence and domain structure of human (HU) E-selectin. Identical amino acids are denoted by an asterisk (*) and gaps are denoted with horizontal lines (–). Domains are denoted by the following abbreviations: Signal peptide, SP; Lectin Domain, Lec; Epidermal growth factor domain, EGF; Complement repeats, CR1–CR6; Transmembrane domain, TM; Cytoplasmic tail, CYT. As noted below, the complement repeats #1 and #4 are absent from porcine E-selectin.

DESCRIPTION OF THE PREFERRED EMBODIMENTS

Figure 2A:
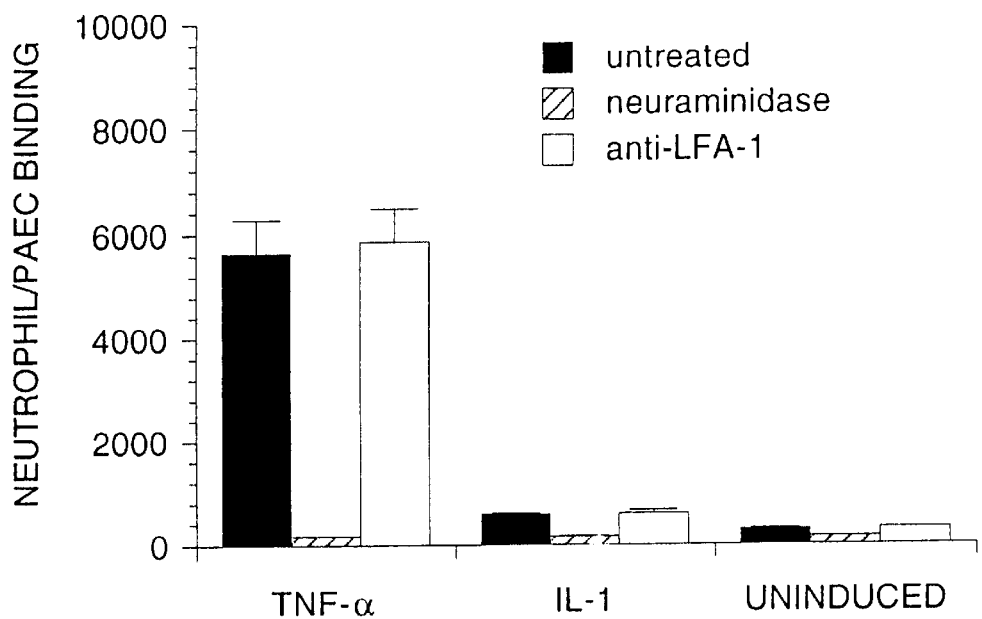
FIGS. 2A–2B. Human neutrophils and HL-60 cells bind to human cytokine-induced PAEC: The binding of calcein-labeled human neutrophils (FIG. 2A) and HL-60 cells (FIG. 2B) to confluent monolayers of cytokine-induced PAEC was determined. Neutrophils and HL-60 cells were incubated in a control buffer (solid bars), treated with neuraminidase (hatched bars) or incubated in the presence of 10 μg/ml anti-LFA-1 (open bars) prior to addition to confluent monolayers of PAEC in 96 well plates. PAEC were incubated (37° C., 4hr) in either medium containing 25 ng/ml human TNFα (TNFα), 20 ng/ml human IL-1 (IL-1), or media alone (UNINDUCED), prior to the addition of human neutrophils or HL-60 cells. Cell binding was determined as described below under the heading "Materials and Methods". Error bars denote standard error of triplicate determinations from a single experiment and are representative of three so performed.

As discussed above, the present invention relates to the cell adhesion protein, E-selectin, and specifically to the porcine E-selectin molecule. The data presented in the examples set forth below demonstrate that human white blood cells bind to porcine endothelial cells via binding to porcine E-selectin. This binding interaction has significant implications for the outcome of xenotransplantation of porcine organs into human recipients, as such binding of white blood cells to endothelial cells is one of the first steps in the pathway leading to cell-mediated rejection of transplanted endothelial cells, and of vascularized tissues and organs containing such cells.

The discovery of porcine nucleic acid sequences encoding porcine E-selectin provides means to reduce the binding of human white blood cells to porcine endothelial cells, as discussed below. Such inhibition will reduce the frequency with which such porcine endothelial cells, and vascularized tissues and organs containing such cells, are rejected following xenotransplantation into human recipients.

In accordance with the invention, as described in the examples presented below, it has been determined that porcine E-selectin is encoded by the coding region of the nucleic acid sequence of SEQ ID NO:1 and has the amino acid sequence set forth in SEQ ID NO:9. In accordance with certain of its aspects, the invention provides isolated nucleic acid molecules, membrane bound and soluble porcine E-selectin proteins and protein fragments, and antibodies related to porcine E-selectin.

The isolated nucleic acid molecules of the invention comprise sequences that are unique to the porcine genome. As used herein, the term "unique to the porcine genome" refers to sequences found in porcine-derived nucleic acid molecules that do not appear in published form as of the filing date of this application, e.g., they are not found in the cDNAs encoding the E-selectins of humans, cows, mice, or dogs.

The isolated nucleic acid molecules of the invention comprise sense sequences of contiguous nucleotides of SEQ ID NO:1. These sense sequences are unique to the porcine genome, and can be used as PCR primers or hybridization probes for the identification and/or isolation of the porcine E-selectin gene from genomic DNA. Antisense sequences of contiguous nucleotides complementary to such sense sequences are also required in order to practice PCR, and may also be used as hybridization probes. In order to be used for such purposes, the sequences of contiguous nucleotides must span a sufficient length. The minimum oligonucleotide length required for specific hybridization (i.e., hybridization under conditions requiring an essentially perfect match of complementary nucleotides wherein the sequence of the probe can be expected to occur only once in the genome of the organism being probed) of both hybridization probes and PCR primers is well known in the art, and is discussed in, for example, Sambrook, et al, 1989, on pages 11.7–11.8. In practice, this span is at least 14 nucleotides, and, preferably, at least 18 nucleotides. Because at least 2 PCR primers are generally required to carry out a PCR reaction, the specificity of the PCR reaction is greater than that of each of the oligonucleotide primers used to drive the reaction.

Another isolated nucleic acid molecule of the invention is a cloned porcine genomic DNA molecule comprising a sequence of nucleotides unique to the porcine genome. This cloned molecule is characterized by hybridizing specifically to an isolated nucleic acid molecule as described in the preceding paragraph. Specific hybridization is used to clone this genomic DNA molecule. This cloning can be accomplished by several methods well known in the art such as by PCR using porcine genomic DNA templates, or by conventional screening of phage libraries of porcine genomic DNA, e.g., by plaque lift filter hybridization.

The isolated nucleic acid molecules of the invention are also useful as means to direct and/or modulate the expression of porcine E-selectin in porcine cells, e.g., by altering the expression of the porcine E-selectin gene. Such modulation may be accomplished by several means well known in the art. Modulation, specifically inhibition, of the expression of any particular gene may be accomplished by the use of antisense nucleic acid molecules or DNA constructions specially engineered to allow gene inactivation as described below for antisense RNAs, antisense oligonucleotides, and gene knockout constructions. For the inhibition of the porcine E-selectin gene, the antisense nucleic acid molecules or DNA constructions will comprise nucleic acid sequences of the nucleic acid molecules of the invention.

Antisense RNAs can be used to specifically inhibit gene expression (see, for example, Eguchi, et al., 1991). Such nucleic acid molecules can be expressed by recombinant transcription units engineered for expression in porcine cells. Such transcription units can be introduced as transgenes into porcine cells, and, when introduced into porcine embryos or embryonic stem cells can be used to generate transgenic pigs.

Antisense nucleic acid molecules in the form of oligonucleotides (including oligonuclotide analogs) and derivatives thereof can also be used to specifically inhibit gene expression, as described, for example, in Cohen, 1989. As described therein, antisense oligonucleotides can be designed and used to inhibit expression of specific genes (Cohen, 1989, pp. 1–6, 53–77).

Such antisense oligonucleotides can be in the form of oligonucleotide analogs, for example, phosphorothioate analogs (Cohen, 1989, pp. 97–117), non-ionic analogs (Cohen, 1989, pp. 79–95), and α-oligodeoxynucleotide analogs (Cohen, 1989, pp. 119–136). Derivatives of oligonucleotides that can be used to inhibit gene expression include oligonucleotides covalently linked to intercalating agents or to nucleic acid-cleaving agents (Cohen, 1989, pp. 137–172), and oligonucleotides linked to reactive groups (Cohen, 1989, pp. 173–196). oligonucleotides and derivatives designed to recognize double-helical DNA by triple-helix formation (Cohen, 1989, pp. 197–210) may also be used to specifically inhibit gene expression.

All of the oligonucleotides and derivatives described above are used by adding them to the fluids bathing the cells in which specific inhibition of gene expression in accordance with the present invention is desired.

Another method by which the expression of specific genes can be inhibited is by genetic manipulations referred to in the art as "gene disruption" or "gene knockout." Gene knockout is a method of genetic manipulation via homologous recombination that has long been carried out in microorganisms, but has only been practiced in mammalian cells within the past decade. These techniques allow for the use of specially designed DNA molecules (gene knockout constructions) to achieve targeted inactivation (knockout) of a particular gene upon introduction of the construction into a cell. The practice of mammalian gene knockout, including the design of gene knockout constructions and the detection and selection of successfully altered mammalian cells, is discussed in numerous publications, including Thomas, et al., 1986; Thomas, et al., 1987; Jasin and Berg, 1988; Mansour, et al., 1988; Brinster, et al., 1989; Capecchi, 1989; Frohman and Martin, 1989; Hasty, et al., 1991; Jeannotte, et al., 1991; and Mortensen, et al., 1992.

Gene knockouts and gene replacements can be achieved in mammalian zygotes through microinjection techniques well known in the art (Brinster, et al., 1989). The introduction of the DNA constructions used to effect gene knockouts into cultured cells is a more common route to the production of knockout cells, tissues, and organs. In those cases where knockout tissues or organs are desired, cultured embryonic stem cells provide a means to introduce the DNA constructions into cells in culture and to generate transgenic animals derived from such engineered cells. Such animals can also be obtained from knockout transgenic zygotes obtained by microinjection as described above.

Thus, in accordance with certain aspects of the invention, the nucleic acid molecules of the present invention are used to generate engineered transgenic animals using techniques known in the art. These techniques include, but are not limited to, microinjection, e.g., of pronuclei, electroporation of ova or zygotes, nuclear transplantation, and/or the stable transfection or transduction of embryonic stem cells.

The most well known method for making transgenic animals is that used to produce transgenic mice by superovulation of a donor female, surgical removal of the egg, injection of the transgene transcription unit into the pronuclei of the embryo, and introduction of the transgenic embryo into the reproductive tract of a pseudopregnant host mother, usually of the same species. See Wagner, U.S. Pat. No. 4,873,191, Brinster, et al., 1985, Hogan, et al., 1986, Robertson 1987, Pedersen, et al., 1990.

The use of this method to make transgenic livestock is also widely practiced by those of skill in the art. As an example, transgenic swine are routinely produced by the microinjection of nucleic acid molecules into pig embryos. See, for example, PCT Publication No. WO92/11757. In brief, this procedure may, for example, be performed as follows. First, the nucleic acid molecules are gel isolated and extensively purified, for example, through an ELUTIP column (Schleicher & Schuell, Keene, N. H.), dialyzed against pyrogen free injection buffer (10 mM Tris, pH7.4+0.1 mM EDTA in pyrogen free water), and used for embryo injection.

Embryos are recovered from the oviduct of a hormonally synchronized, ovulation induced sow, preferably at the pronuclear stage. They are placed into a 1.5 ml microfuge tube containing approximately 0.5 ml of embryo transfer media (phosphate buffered saline with 10% fetal calf serum). These are centrifuged for 12 minutes at 16,000× g in a microcentrifuge. Embryos are removed from the microfuge tube with a drawn and polished Pasteur pipette and placed into a 35 mm petri dish for examination. If the cytoplasm is still opaque with lipid such that the pronuclei are not clearly visible, the embryos are centrifuged again for an additional 15 minutes.

Embryos to be microinjected are placed into a drop of media (approximately 100 μl) in the center of the lid of a 100 mm petri dish. Silicone oil is used to cover this drop and to fill the lid to prevent the medium from evaporating. The petri dish lid containing the embryos is set onto an inverted microscope equipped with both a heated stage (37.5–38° C.) and Hoffman modulation contrast optics (200X final magnification). A finely drawn and polished micropipette is used to stabilize the embryos while about 1–2 picoliters of injection buffer containing approximately 200–500 copies of the purified transgene transcription unit is delivered into the nucleus, preferably the male pronucleus, with another finely drawn and polished micropipette. Embryos surviving the microinjection process as judged by morphological observation are loaded into a polypropylene tube (2 mm ID) for transfer into the recipient pseudopregnant sow.

Offspring are tested for the presence of the transgene by isolating genomic DNA, e.g., from tissue removed from the tail of each piglet, and subjecting about micrograms of this genomic DNA to nucleic acid hybridization analysis with a transgene specific probe.

Another commonly used technique for generating transgenic animals involves the genetic manipulation of embryonic stem cells (ES cells) as described in PCT Patent Publication No. WO 93/02188 and Robertson, 1987. In accordance with this technique, ES cells are grown as described in, for example, Robertson, 1987, and in U.S. Pat. No. 5,166,065 to Williams et al. Genetic material is introduced into the embryonic stem cells by, for example, electroporation according, for example, to the method of McMahon, et al., 1990, or by transduction with a retroviral vector according, for example, to the method of Robertson, et al., 1986, or by any of the various techniques described by Lovell-Badge, 1987.

Chimeric animals are generated as described, for example, in Bradley, 1987. Briefly, genetically modified ES cells are introduced into blastocysts and the modified blastocysts are then implanted in pseudo-pregnant female animals. Chimeras are selected from the offspring, for example by the observation of mosaic coat coloration resulting from differences in the strain used to prepare the ES cells and the strain used to prepare the blastocysts, and are bred to produce non-chimeric transgenic animals.

Other methods for the production of transgenic animals are disclosed in U.S. Pat. No. 5,032,407 to Wagner et al., and PCT Publication No. WO90/08832.

The practice of gene knockout in embryonic stem cells, and the generation of engineered animals from such cells, is discussed in numerous publications, including Thomas, et al., 1987; Robertson, 1987; Mansour, et al., 1988; Capecchi, 1989; Frohman and Martin, 1989; Hasty, et al., 1991; Jeannotte, et al., 1991; Mortensen, et al., 1992; Thomas, et al., 1992; and PCT Patent Publication No. WO 93/02188.

Among other applications, transgenic pigs prepared in accordance with the invention are useful as model systems for testing the xenotransplantation of their engineered cells, tissues, or organs and as sources of engineered cells, tissues, or organs for xenotransplantation. The lack of expression of porcine E-selectin on the endothelial cells of the transgenic pigs will provide enhanced protection from rejection following xenotransplantation of those cells, or of tissues and organs containing those cells, into recipient animals, e.g., humans. In addition to their use in producing tissues, and organs for transplantation, the nucleic acid molecules of the invention can also be used to directly engineer cultured porcine endothelial cells for subsequent use in transplantation.

The nucleic acid molecules of the invention can also be used to express porcine E-selectin proteins for subsequent purification and use. Recombinant DNA methods for the production of recombinant proteins are well known in the art, as are methods for the purification of such proteins (see, for example, Ausubel, et al., 1992; Goeddel, 1990; Harris and Angal, 1989; and Deutscher, 1990). The production of soluble porcine E-selectin by such means is described below under the heading "Materials and Methods, and under the subheadings "generation of vectors directing the expression of soluble porcine E-selectin", "generation of stably transfected cells secreting porcine E-selectin", and "purification and characterization of soluble porcine E-selectin protein", and is also described below in Example 6. Preferred uses of such proteins include the use of soluble porcine E-selectin as an immunogen for the purpose of raising anti porcine E-selectin antibodies, or as an antigen for use in an immunoassay as described below under the heading "Materials and Methods", and under the subheading "ELISA screen for anti-porcine E-selectin antibodies".

The present invention provides recombinant expression vectors which include synthetic or cDNA-derived DNA fragments encoding porcine E-selectin. The nucleotide sequence coding for porcine E-selectin can be inserted into an appropriate expression vector, i.e., a vector that contains the necessary elements for the transcription and translation of the inserted protein-coding sequence. The necessary transcriptional and translational signals can also be supplied by the native gene and/or its flanking regions. A variety of host vector systems may be utilized to express the protein-coding sequence. These include, but are not limited to, mammalian cell systems infected with virus (e.g., vaccinia virus, adenovirus, retroviruses, etc.); mammalian cell systems transfected with plasmids; insect cell systems infected with virus (e.g., baculovirus); microorganisms such as yeast containing yeast expression vectors, or bacteria transformed with bacteriophage DNA, plasmid DNA, or cosmid DNA (see, for example, Goeddel, 1990).

Useful expression vectors for bacterial use can comprise a selectable marker and bacterial origin of replication derived from commercially available plasmids comprising genetic elements of the well-known cloning vector pBR322 (American Type Culture Collection, 12301 Parklawn Drive, Rockville, Md. 20852, United States of America; ATCC Accession No. 37017). These pBR322 "backbone sections," or functionally equivalent sequences, are combined with an appropriate promoter and the structural gene to be expressed. Promoters commonly used in recombinant microbial expression vectors include, but are not limited to, the lactose promoter system (Chang, et al., 1978), the tryptophan (trp) promoter (Goeddel, et al., 1980) and the tac promoter, or a fusion between the tac and trp promoters referred to as the trc promoter (Maniatis, 1982). Preferred bacterial expression vectors include, but are not limited to, vector pSE420 (Invitrogen Corporation, San Diego, Calif.). This vector harbors the trc promoter, the lacO operon, an anti-terminator sequence, the g10 ribosome binding sequence, a translation terminator sequence, the lacIq repressor, the ColE1 origin of replication, and the ampicillin resistance gene.

Recombinant porcine E-selectin may also be expressed in fungal hosts, preferably yeast of the Saccharomyces genus such as $S.$ $cerevisiae$. Fungi of other genera such as Aspergillus, Pichia or Kluyveromyces may also be employed. Fungal vectors will generally contain an origin of replication from the 2 $\mu$m yeast plasmid or another autonomously replicating sequence (ARS), a promoter, DNA encoding porcine E-selectin, sequences directing polyadenylation and transcription termination, and a selectable marker gene. Preferably, fungal vectors will include an origin of replication and selectable markers permitting transformation of both $E.$ $coli$ and fungi.

Suitable promoter systems in fungi include the promoters for metallothionein, 3-phosphoglycerate kinase, or other glycolytic enzymes such as enolase, hexokinase, pyruvate kinase, glucokinase, the glucose-repressible alcohol dehydrogenase promoter (ADH2), the constitutive promoter from the alcohol dehydrogenase gene, ADH1, and others. See, for example, Schena, et al. 1991. Secretion signals, such as those directing the secretion of yeast a-factor or yeast invertase, can be incorporated into the fungal vector to promote secretion of a soluble porcine E-selectin into the fungal growth medium. See Moir, et al., 1991.

Preferred fungal expression vectors can be assembled using DNA sequences from pBR322 for selection and replication in bacteria, and fungal DNA sequences, including the ADH1 promoter and the alcohol dehydrogenase ADH1 termination sequence, as found in vector PAAH5 (Ammerer, 1983). The ADH1 promoter is effective in yeast in that ADH1 mRNA is estimated to be 1–2% of total poly(A) RNA.

Various mammalian or insect cell culture systems can be employed to express recombinant porcine E-selectin. Suitable baculovirus systems for production of heterologous proteins in insect cells are reviewed by Luckow, et al., 1988. Examples of suitable mammalian host cell lines include the COS cell of monkey kidney origin, mouse L cells, murine C127 mammary epithelial cells, mouse Balb/3T3 cells, Chinese hamster ovary cells (CHO), human 293 EBNA and HeLa cells, myeloma, and baby hamster kidney (BHK) cells. Mammalian expression vectors may comprise non-transcribed elements such as origin of replication, a suitable promoter and enhancer linked to the porcine E-selectin gene to be expressed, and other 5' or 3' flanking sequences such as ribosome binding sites, a polyadenylation sequence, splice donor and acceptor sites, and transcriptional termination sequences.

The transcriptional and translational control sequences in mammalian expression vector systems to be used in transforming vertebrate cells may be provided by viral sources. For example, commonly used promoters and enhancers are derived from Polyoma virus, Adenovirus, Simian Virus 40 (SV40), and human cytomegalovirus, including the cytomegalovirus immediate-early gene 1 promoter and enhancer (CMV).

Particularly preferred eukaryotic vectors for the expression of porcine E-selectin are pAPEX-1 and pAPEX-3, as described below under the heading "Materials and Methods," and under the subheadings "assays for binding of human neutrophils and HL-60 cells to porcine E-selectin transfected COS cells," and "generation of vectors directing the expression of soluble porcine E-selectin". A particularly preferred host cell for the expression of inserts in the pAPEX-3 vector is the human 293 EBNA cell line (Invitrogen, San Diego, Calif.).

Another preferred eukaryotic vector for the expression of porcine E-selectin is pcDNAI/Amp (Invitrogen Corporation, San Diego, Calif.). The pcDNAI/Amp expression vector contains the human cytomegalovirus immediate-early gene I promoter and enhancer elements, the Simian Virus 40 (SV40) consensus intron donor and acceptor splice sequences, and the SV40 consensus polyadeaylation signal. This vector also contains an SV40 origin of replication that allows for episomal amplification in cells (e.g., COS cells, MOP8 cells, etc.) transformed with SV40 large T antigen, and an ampicillin resistance gene for propagation and selection in bacterial hosts.

Purified porcine E-selectin is prepared by culturing suitable host/vector systems to express the recombinant translation products of the nucleic acid molecules of the present invention, which are then purified from the culture media or cell extracts of the host system, e.g., the bacteria, insect cells, fungal, or mammalian cells. Fermentation of fungi or mammalian cells that express soluble porcine E-selectin protein containing a histidine tag sequence (comprising a string of at least 5 histidine residues in a row) as a secreted product greatly simplifies purification. Such a histidine tag sequence enables binding under specific conditions to metals s, as nickel, and thereby to nickel columns for purification. Specific examples of the generation of a porcine E-selectin protein containing such a histidine tag sequence and its purification is set forth below under the head "Materials and Methods", and under the subheadings "generation of vectors directing the expression of soluble porcine E-selectin", and "purification and characterization of soluble porcine E-selectin protein".

In general terms, the purification of recombinant porcine E-selectin is performed using a suitable set of concentration, fractionation, and chromatography steps well known in the art (see, for example, Deutscher, 1990; and Harris and Angal, 1989). For recombinant porcine E-selectins requiring correct disulfide bond formation for full biological activity, denaturation of the purified protein followed by chemical-mediated refolding under reducing conditions can be done to promote proper disulfide interactions.

Porcine E-selectin proteins purified from bodily fluids of transgenic animals engineered to produce the porcine E-selectins of the invention are also with the scope of the invention, as are porcine E-selectins that are produced in part or entirely by chemical synthesis.

Porcine E-selectins synthesized in recombinant culture and subsequently purified may be characterized by the presence of contaminating components. These components may include proteins or other molecules in amounts and of a character which depend on the production and purification processes. These components will ordinarily be of viral, prokaryotic, eukaryotic, or synthetic origin, and preferably are present in innocuous contaminant quantities, on the order of less that about 1% by weight. Recombinant cell culture, however, enables the production of porcine E-selectins relatively free of other proteins that may normally be associated with the protein as it is found in nature.

As discussed above, certain aspects of the present invention relates to the use of anti porcine E-selectin antibodies or soluble E-selectin protein (collectively referred to hereinafter as therapeutic E-selection agents") in treating patients suffering from xenotransplant rejection. The therapeutic E-selectin agents are used in an amount effective to achieve blood concentrations equivalent to in vitro concentrations that substantially reduce (e.g., reduce by at least about 50% the binding of human test cells expressing the human E-selectin binding ligand, such as PBLs, neutrophils, and HL-60 cells, to cells expressing porcine E-selectin, such as TNFα treated porcine endothelial cells. Reduction of the binding of human test cells to cells expressing porcine E-selectin can be measured by methods well known in the art such as, for example, by the assay described below under the heading "assays for neutrophil/HL-60 binding to PAEC".

To achieve the desired reductions in binding, the therapeutic E-selectin agents can be administered in a variety of unit dosage forms. The dose will vary according to the particular agent. For example, different antibodies may have different masses and/or affinities, and thus require different dosage levels. Antibodies prepared as Fab' or F(ab')$_2$ fragments will also require differing dosages than the equivalent intact immunoglobulins, as they are of considerably smaller mass than intact immunoglobulins, and thus require lower dosages to reach the same molar levels in the patient's blood.

The dose will also vary depending on the manner of administration, the particular symptoms of the patient being treated, the overall health, condition, size, and age of the patient, and the judgment of the prescribing physician. Dosage levels of the therapeutic E-selectin agents for human subjects are generally between about 1 mg per kg and about 100 mg per kg per patient per treatment, and preferably between about 5 mg per kg and about 50 mg per kg per patient per treatment. In terms of plasma concentrations, the therapeutic E-selectin agent concentrations are preferably in the range from about 25 µg/ml to about 500 µg/ml.

Subject to the judgement of the physician, a typical therapeutic treatment includes a series of doses, which will usually be administered concurrently with the monitoring of clinical endpoints such as xenotransplant biopsies, or measures of organ function, such as, for example, for xenotransplanted kidneys, BUN levels proteinuria levels, etc., with the dosage levels adjusted as needed to achieve the desired clinical outcome.

The therapeutic E-selectin agents of the present invention can be used in therapeutic compositions to treat episodes of xenograft rejection. Such treatment will result in the reduction of the severity of the rejection episode. For such application, purified therapeutic E-selectin agents can be administered to a patient, e.g., human, in a variety of ways. Thus, therapeutic E-selectin agents can be given by bolus injection, continuous infusion, sustained release from implants, or other suitable techniques.

Formulations suitable for injection are found *Remington's Pharmaceutical Sciences*, Mack Publishing Company, Philadelphia, Pa., 17th ed. (1985). Such formulations must be sterile and non-pyrogenric, and generally will include purified therapeutic E-selectin agents in conjunction with a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like.

In one preferred embodiment, the therapeutic E-selectin agent is formulated as a lyophilizate using appropriate excipient solutions (e.g., sucrose, albumin) as diluents. The amount and frequency of administration will depend, of course, on such factors as the nature and severity of the rejection episode being treated, the desired response, the condition of the patient, and so forth.

The formulations of the invention can be distributed as articles of manufacture comprising packaging material and the therapeutic E-selectin agents. The packaging material will include a label which indicates that the formulation is for use in the treatment of porcine xenotransplant rejection.

Hybridomas producing the monoclonal antibodies of the invention, i.e., monoclonal antibodies reactive with porcine E-selectin, but not with human E-selectin, can be obtained using purified porcine E-selectin as an immunogen followed by screening. Such screening is carried out to identify hybridomas producing antibodies with the desired properties, and can be carried out using appropriate immunoassays. Examples of appropriate immunoassays are the ELISA described below under the heading "Materials and Methods, and under the subheading "ELISA screen for anti-porcine E-selectin antibodies". This ELISA can be used to identify hybridomas producing antibodies that bind to porcine E-selectin. A simple modification of this ELISA (consisting of substituting soluble human E-selectin for soluble porcine E-selectin) can be used to identify those of the hybridomas producing antibodies that bind to porcine E-selectin in which the antibodies do not bind to human E-selectin.

General methods for the immunization of animals this case with porcine E-selectin), isolation of antibody producing cells, fusion of such cells with immortal cells (e.g., myeloma cells) to generate hybridomas secreting monoclonal antibodies, screening of hybridoma supernatants for reactivity and/or lack of reactivity of secreted monoclonal antibodies with particular antigens (in this case reactivity with porcine E-selectin but not with human E-selectin), the preparation of quantities of such antibodies in hybridoma supernatants or ascites fluids, and for the purification and storage of such monoclonal antibodies, can be found in numerous publications. These include: Coligan, et al., eds. *Current Protocols In Immunology*, John Wiley & Sons, New York, 1992; Harlow and Lane, *Antibodies. A Laboratory Manual*, Cold Spring Harbor Laboratory, New York, 1988; Liddell and Cryer, *A Practical Guide To Monoclonal Antibodies*, John Wiley & Sons, Chichester, West Sussex, England, 1991; Montz, et al., 1990; Wurzner, et al., 1991; and Mollnes, et al., 1988.

The present invention also includes porcine E-selectins and anti porcine E-selectin antibodies with or without associated native patterns of glycosylation. For example, expressing proteins recombinantly in bacteria such as E coli provides non-glycosylated molecules, while expressing porcine E-selectins or anti porcine E-selection antibodies in mammalian cells can provide glycosylated molecules.

As used herein, the term "antibodies" refers to immunoglobulins produced in vivo, as well as those produced in vitro by a hybridoma, and antigen binding fragments (e.g., Fab' preparations) of such immunoglobulins, as well as to recombinantly expressed antigen binding proteins, including immunoglobulins, chimeric immunoglobulins, "humanized" immunoglobulins, antigen binding fragments of such immunoglobulins, single chain antibodies, and other recombinant proteins containing antigen binding domains derived from immunoglobulins. Publications describing methods for the preparation of such antibodies, in addition to those listed immediately above, include: Reichmann, et al., 1988; Winter and Milstein, 1991; Clackson, et al., 1991; Morrison, 1992; Haber, 1992; and Rodrigues, et al., 1993.

Diagnostic use of the anti porcine E-selectin antibodies of the invention can be carried out by assaying the patient's blood for levels of porcine E-selectin. Assays for porcine E-selectin levels may be by RIA, ELISA or other suitable immunoassay using the anti porcine E-selectin antibodies of the invention. General methods for performing such assays are set forth in Coligan, et al., 1992. Blood porcine E-selectin levels must be monitored at regular intervals, e.g., daily or weekly, and changes in such levels recorded. Any distinct increase in porcine E-selectin levels in the patient's blood is an indication that the porcine endothelium is being activated, and may indicate the onset of a rejection episode.

An alternative test for rejection, (or a test providing confirmation of the occurrence of rejection as indicated by measurement of soluble E-selectin levels) may be obtained by monitoring porcine organ function or by biopsy and histopathological examination of the porcine organ. Such examination will be carried out in order detect the typical manifestations of transplant rejection e.g., cellular infiltrates, inflammation, and necrosis. In accordance with the invention, the histopathological examination of xenotransplanted organ biopsy tissues will also include the use of the antibodies of the invention to detect the levels of expression of porcine E-selectin on the surfaces of the cells of the biopsied tissues of xenotransplanted organ. High levels of such express (compared to levels on non-transplanted control tissue samples) are indicative of xenotransplant rejection.

Although specific embodiments of the invention described and illustrated herein, it is to be understood that modifications can be made without departing from the invention's spirit and scope.

For example, the nucleotide sequences of the porcine E-selectin-encoding nucleic acid molecules of the invention may be modified by creating nucleic acid mutations which do not significantly change the encoded amino acid sequences. Such mutations include third nucleotide changes in degenerate codons (and other "silent" mutations that do not change the encoded amino acid sequence).

Other such mutations within the scope of invention and considered as equivalents of the specific embodiments set forth herein include those which result in a highly conservative amino acid substitution for an encoded amino acid while leaving the leucocyte binding characteristics of the porcine E-selectin molecule essentially unchanged. Such silent or highly conservative mutations are included within the scope of the invention.

Also included are:

1) Nucleotide and amino acid sequences comprising changes that are found as naturally occurring allelic variants of the porcine E-selectin gene;
2) Sequences which have been truncated so as to only encode the mature porcine E-selectin polypeptide, i.e., a porcine E-selectin polypeptide without the amino terminal leader sequence that directs the protein to its typical transmembrane orientation in the cell, indicated by negative amino acid numbers in SEQ ID NO:9;
3) Sequences in which the E-selectin amino terminal leader sequence has been altered, e.g., substituted with a different leader;
4) Sequences in which a peptide "tag" sequence has been inserted or added on to enable the ready identification and/or purification of recombinant proteins. Such tags include the FLAG epitope (which enables specific binding to anti-FLAG antibodies) and a histidine tag sequence, as described above;
5) Sequences that have been altered to produce a soluble porcine E-selectin protein by, for example, truncation near amino acid number 405 of SEQ ID NO:9 as described below under the heading "Materials and Method" and the sub-heading "generation of vectors directing the expression of soluble porcine E-selectin." Such soluble selectin proteins and sequence alterations have also been described for the human E-selectin molecule. The generation of recombinant soluble human E-selectin molecules is disclosed in Lobb, et al., 1991, and PCT patent publication No. WO 93/07268.

Without intending to limit it in any manner, the present invention will be more fully described by the following examples. Materials and methods used in various of the examples are as follows.

MATERIALS AND METHODS

Materials: A monoclonal antibody to human LFA-1 (clone 25.3) was obtained from AMAC Inc, Westbrook Minn. Human TNFα and IL-1 were obtained from Collaborative Biomedical Products, Bedford Mass. Dulbecco's modified Eagles medium (DMEM) and RPMI-1640 medium were purchased from JRH Biosciences, Lenexa Kans. Fetal bovine serum (FBS) was purchased from Harlan, Indianapolis Ind. Sterilie Hank's balanced salt solution (HBSS) and phosphate buffer saline (PBS) were purchased from Bio Whittaker, Walkersville Md. Calcein AM was obtained from Molecular Probes, Eugene Oreg. Neuraminidase was purchased from Boehringer Mannheim, Indianapolis Ind. All other reagents were of analytical grade or better and purchased from Sigma Chemical Co., Saint Louis Mo., unless otherwise specified.

Cell culture: Porcine aortic endothelial cells (PAED were obtained at passage 1 (Cell Systems, Kirkland Wash.) a maintained in DMEM containing 10% FBS, penicillin 100 U/ml, and streptomycin 100 $\mu$g/ml (pen/strep, JRH Biosciences, Lenexa KS), hereinafter referred to as D10 medium. PAEC were at passage 2–4 in all assays. For cell binding assays, PAEC were removed from culture flasks with trypsin EDTA and replated onto 96 well culture dishes at a density of $1\times10^4$ cells/well. The human promyelocytic leukemia cell line HL-60 was obtained from the American Type Culture Collection (ATCC), Rockville, Md. and maintained in D10.

Assays for Neutrophil/HL-60 binding to PAEC: Confluent monolayers of PAEC in 96 well plates were incubated (4 hr, 37° C.) in 200 $\mu$l/well DMEM alone, DMEM containing 25 ng/ml human TNFα, or DMEM containing 10 ng/ml human IL-1. During this incubation, human neutrophils were isolated from 60 ml of human blood obtained from a healthy donor using the manufacturer's protocol (Polymorphoprep, Oslo, Norway), or HL-60 cells were spun down from culture medium.

The isolated neutrophils or HL-60 cells were washed 2× with HBSS, resuspended in HBSS containing 1% BSA (HBSS/BSA) at a final concentration of $3\times10^6$ cells/ml, incubated (30 min, 37° C.) in the cytoplasmic indicator calcein AM (10 $\mu$M), washed 2× with HBSS and resuspended $3\times10^6$ cells/ml in HBSS/BSA. Prior to addition to PAEC monolayers, the purified human neutrophils or HL-60 cells were incubated (30 min, 37° C.) in either, HBSS/BSA, HBSS/BSA containing 0.25 U/ml neuraminidase, or HBSS/BSA containing 10 $\mu$g/ml anti-LFA-1 mAb.

Following this incubation, the neutrophils or HL-60 cells were washed 2× with HBSS/BSA and resuspended to 3 $\times10^6$ cells/ml. PAEC monolayers were then washed 3× with HBSS/BSA and calcein-loaded human neutrophils or HL-60 cells were added at $3\times10^5$ cells/well. The plates were centrifuged briefly (250× g, 1 minute), incubated in the dark for 5 min at 37° C. and then centrifuged upside down 250× g for 3 minutes. The media and unbound neutrophils or HL-60 cells were removed from the plate and the bound cells were lysed by the addition of 1% SDS (100 $\mu$l/well) in HBSS. Neutrophil or HL-60 cell binding was determined by measuring the release of calcein from bound neutrophils or HL-60 cells into the lysis buffer using a Cytofluor 2350 (Millipore, Bedford Mass.—excitation wavelength=485 nm, emission wavelength=530 nm). Background fluorescence was determined from wells containing PAEC that did not receive labeled neutrophils or HL-60 cells. Cloning and Sequencing: PAEC were grown to near confluence and stimulated with human TNFα (20 nag/ml) in D10 for 4 hours at 37° C. Total RNA was isolated from these cells using the acid/guanidinium thiocyanate technique (Chomczynski and Sacchi, 1987). Ten micrograms of total RNA was heated at 65° C. for 3 min and quenched on ice before first strand cDNA synthesis was carried out for 1 hr at 37° C. in the following reaction mixture: 10 mM Tris-HCl (pH 8.3), 50 mM KCl, 1.5 mM MgCl$_2$, 10 mM dithiothreotol, 0.25 mM of each dNTP, 0.5 $\mu$g oligo dT$_{16}$, and 20 U of avian myeloblastosis virus reverse transcriptase (Seikagaku Inc, Rockville Md.).

The cDNA pool (5 $\mu$l of first strand cDNA reaction mixture) was used as a template in a 100 $\mu$l PCR reaction under the following reaction conditions: 50 mM KCl, 10 mM Tris-HCL (pH 9.0), 1.5 mM MgCl$_2$, 0.1% (w/v) gelatin, 1% Triton X-100, 200 $\mu$M each dNTP, 2.5 U Taq DNA polymerase (Perkin Elmer Cetus, Norwalk Conn.) using 25 pmol of each primer—oligo 138 (SEQ ID NO:2) and oligo 139 (SEQ ID NO:3). PCR amplification was performed for 40 cycles (95° C. for 1 min, 42° C. for 2 min, 72° C. for 2 min) followed by 1 cycle at 72° C. for 10 min.

The resulting approximately 150 base pair PCR fragment (referred to hereinafter as the "150 bp fragment") was cloned into the pCRII vector using the T/A cloning system (which includes the PCRII vector) as described by the manufacturer (Invitrogen, San Diego Calif.). The 150 bp fragment in pCRII was subjected to sequence analysis (Sanger, et al., 1977). Comparison of the non-oligonucleotide derived sequence of this PCR fragment (nucleotide 357 through nucleotide 454 of SEQ ID NO:1) with those of human and mouse E-selectin confirmed that the fragment encoded an amino acid sequence that was homologous to the lectin binding domains of the human and mouse proteins.

The 150 base pair fragment was subsequently used to screen a UNI-ZAP XR cDNA library (Stratagene, La Jolla Calif.) constructed from PAEC RNA prepared following stimulation of PAEC with human TNFα as described above. The library was plated and screened as recommended by the supplier's protocol with only minor modifications.

Briefly, $1\times10^6$ phage were isolated on nitrocellulose lifts which were subsequently denatured, neutralized, and air dried. Denatured filters were prehybridized in BSA/SDS buffer (Church and Gilbert, 1984) for 2 hr at 60° C. before addition of the 150 base pair fragment which had been $^{32}P$ labeled with the PRIME IT random primer kit (Stratagene, La Jolla Calif.) to a specific activity of $1\times10^9$ CPM/μg of DNA. Membranes were hybridized at 60° C. overnight and subsequently washed using the following conditions: two-30 min washes with 2× SSC/0.1% SDS at room temperature followed by two-30 min washes with 0.5× SSC/0.1% SDS at 60° C.

Positive plaques present on duplicate lifts, were purified and plasmid (BLUESCRIPT SK⁻ phagemid) DNA rescued in accordance with the instructions of the UNI-ZAP XR vector manufacturer (Stratagene, La Jolla Calif). Both strands of a putative full-length clone of approximately 3.4 kb (designated "porcine E-selectin/pBLUESCRIPT SK⁻") were sequenced through the coding region using the chain termination method (Sanger, et al., 1977). The DNA template was primed with vector primers flanking the multiple cloning site of the BLUESCRIPT SK⁻ vector or primers constructed subsequent to the initial sequencing runs from the internal cDNA sequence. The sequence obtained is set forth as SEQ ID NO:1.

Assays for binding of human neutrophils and HL-60 cells to porcine E-selectin transfected COS cells: COS7 cells (Designation CRL 1651, ATCC, Rockville, Md.) were transiently transfected with either the eukaryotic expression vector pAPEX-1 alone or pAPEX-1 containing the full-lengthporcine E-selectin cDNA (pAPEX-1/pE-selectin Briefly, a 3.5 kb NotI-XhoI fragment (from plasmid vector porcine E-selectin/pBLUESCRIPT SK⁻) containing the porcine E-selectin cDNA was cloned into the NotI/XhoI sites of the polylinker in the expression vector pAPEX-1.

pAPEX-1 (SEQ ID NO:4) is a derivative of the vector pcDNAI/Amp (Invitrogen, San Diego Calif.) which was modified as follows to increase protein expression in mammalian cells. First, since the intron derived from the gene encoding the SV40 small-t antigen has been shown to decrease expression of upstream coding regions (Evans and Scarpulla, 1989), this intron was removed from pcDNAI/Amp by digestion with XbaI plus HvaI, followed by treatment with the Klenow fragment of DNA polymerase and all four dNTPs. The resulting blunt ended 4.2 kb fragment was gel purified and self ligated to yield a closed circular plasmid.

A 5'-untranslated region adenovirus/immunoglobulin hybrid intron was introduced into the plasmid by replacing a 0.5 kb NdeI-NotI fragment with the corresponding 0.7 kb NdeI-NotI fragment from the vector pRc/CMV7SB (obtained from Dr. Joseph Goldstein, University of Texas Southwest Medical Center, Dallas, Tex.). Finally, the resulting CMV promoter expression cassette was shuttled in an NdeI-SfiI fragment into the vector pGEM-4Z (Promega, Madison Wis.) by ligation to an NdeI-SfiI fragment (containing pGEM-4Z) obtained from a pGEM based expression vector containing a CMV-promoter and an SV40 origin of replication (Davis, et al., 1991).

COS-7 cells were transfected using the DEAE-dextran method. Briefly, COS-7 cells were plated at a density of $2.5\times10^6$ cells per 100 mm tissue culture dish. The cells were transfected 24 hr later using 5 ml serum-free RPMI 1640 medium containing 0.4 mg/ml DEAE-dextran, 100 μM chloroquine, 2 mM glutamine, 25 μg/ml bovine insulin, 25 μg/ml human transferrin, 25 ng/ml sodium selenite, and 1 μg/ml DNA. After incubation at 37° C. for 3.5 hr, the transfection medium was aspirated and replaced with 10% DMSO in PBS for 2 min. The cells were rinsed once with serum-free DMEM and then cultured for 24 hr in D10. On day 2, the cells were harvested using trypsin and plated in a 96 well plate at $1\times10^4$ cells/well. The cells were assayed for the ability to bind human neutrophils and HL-60 cells on day 4 as described above.

Generation of vectors directing the expression of soluble porcine E-selectin: PCR was performed using the plasmid pAPEX-1/pEselectin (described above) as template and oligo 446 (SEQ ID NO:5) and oligo 483 (SEQ ID NO:6) as primers. The approximately 520 bp PCR product was purified using GENE CLEAN and digested with SphI plus EcoRI. The resulting approximately 275 bp band was gel purified and ligated into the vector pGEM-7Zf(+) (Promega, Madison Wis.) to yield the plasmid pGEM-7Zf(+)446/483. The sequence of the cloned fragment of the PCR product was verified by the Sanger dideoxy chain termination method to contain the sequence set forth below as SEQ ID NO:7.

The vector pAPEX-3/spE-selectin+His (directing the expression of soluble porcine E-selectin containing a carboxyl terminal tag of six histidine residues to facilitate purification by nickel affinity chromatography) was constructed by ligating together: a 8973 bp NotI/Sse8337I fragment obtained from pAPEX-3/pE-selectin, a 1551 bp NotI/SphI fragment from pAPEX-3/pE-selectin, and a 264 bp SphI/Sse8337I fragment from pGEM7Zf(+)446/483.

Vector pAPEX-3/pE-selectin was constructed by a three-way ligation of a 4851 bp MluI/XhoI fragment from the vector pAPEX-1/pE-selectin (described above) with a 1144 bp MluI/SI fragment from pDR2b and a 6735 bp SpeI/SalI fragment from APEX-3.

Vector pAPEX-3 (SEQ ID NO:8) was constructed by a three-way ligation of a 1041 bp MluI/BamHI fragment of vector pRc/CMV7SC (obtained from Dr. Joseph Goldstein, University of Texas Southwest Medical Center, Dallas, Tex.; an identical fragment, corresponding to nucleotides 1 to 1041 of SEQ ID NO:4, may be obtained from vector pRc/CMV7SB, referred to above) ligated with a 6747 BamHI/SpeI fragment and a 1144 bp MluI/SpeI fragment, each obtained from vector pDR2b.

Vector pDR2b was constructed by self-ligation of an 8343 bp DNA fragment which was purified by gel electrophoresis after ClaI/AccI digestion of vector pDR2 (Promega Corporation, Madison, Wis.) and treatment of the digestion products with the Klenow fragment of DNA polymerase and all four dNTPs to produce blunt ends.

Vector pAPEX-3 (SEQ ID NO:8, discussed above) contains a CMV promoter followed by a hybrid adenovirus/immunoglobulin intron followed by a polylinker cloning site followed by an SV40 virus polyadenylation sequence. Additionally, APEX-3 contains a gene cassette conferring hygromycin B resistance to mammalian cells, and the Epstein Barr virus origin of replication (oriP) to allow replication and maintenance as a stable episome in cells expressing Epstein Barr virus nuclear antigen (EBNA).

Generation of stably transfected cells secreting porcine E-selectin. 293-EBNA cells, (Invitrogen, San Diego, Calif.) were maintained in medium A (Dulbecco's Modified Eagle's Medium (DMEM) supplemented with 10% (v/v) heat-inactivated fetal calf serum, 100 U/mL penicillin, and 100 ug/ml streptomycin) containing 250 μg/ml G-418. On day 0, cells were plated at 1.0×10$^6$ cells per 60 mm dish. On day 1, the cells were washed twice with DMEM, and refed 0.5 ml DMEM.

TRANSFECTAM reagent (15 μL, Promega Corporation, Madison, Wis.) was added to 0.5 mL DMEM and mixed by pipetting. This TRANSFECTAM in DMEM mixture was next added to 5 ug DNA (pAPEX-3/spE-selectin+His) in 0.5 ml DMEM, mixed by pipetting, and the total 1 mL volume was added to a plate of cells. After incubation for 4 hours at 37° C., the dishes were washed twice with DMEM and refed medium A. On day 2, the cells were refed medium A supplemented with 250 μg/ml G-418 and 300 U/ml hygromycin B. After 7 days all surviving cells were pooled and maintained as cell line 50-A2.

Purification and characterization of soluble porcine E-selectin protein. 50-A2 cells from one confluent 175 cm$^2$ flask were seeded into ten 175 cm$^2$ flasks in 30 mL medium B (medium A containing 250 μg/ml G-418 plus 300 U/ml hygromycin B). The cells were grown to confluence over 7 days with one refeeding. The conditioned medium B was stored at 4° C. until purification. When cells reached confluence, they were refed 30 mL EX-CELL 300 medium (JRH Biosciences, Lexena, Kans.) every 3 to 4 days for a total of 14 days.

Several purification runs were performed, each using 600 ml of conditioned medium B or conditioned EX-CELL 300 medium. The 600 mL of medium was concentrated using a stirred cell fitted with a YM10 membrane (Amicon, Inc., Beverly, Mass.) to a final volume of approximately 50 mL.

Nickel charged resin was prepared by washing iminodiacetic acid/sepharose 6B fast flow resin (Sigma Chemical Company, St. Louis, Mo.) with 7 volumes each of: 1) water; 2) 50 mM NiSO$_4$; and 3) buffer B (20 mM Tris, 500 mM NaCl, 5 mM imidazole, pH 8.0). Each wash was for 30 minutes with rocking to maintain the resin in suspension, followed by centrifugation at 1000 rpm for 5 minutes to pellet the resin.

For binding of the histidine tagged soluble porcine E-selectin, 25 mL concentrated medium was mixed with 3.5 ml 8× buffer B and approximately 1 ml packed volume of NiSO$_4$ charged resin. The medium was incubated for 90 minutes at room temperature with rocking. The resin was removed by centrifugation, and washed twice with 20 ml buffer B. The resin was next resuspended in 10 ml buffer B and poured into a column (BioRad Laboratories, Hercules, Calif.). The column (2 mL settled resin volume) was washed with 35 column volumes buffer B followed by 20 column volumes buffer W (20 mM Tris, 500 mM NaCl, 30 mM imidazole, pH 8.0). Finally, the bound protein was eluted with 4 column volumes of buffer E (20 mM Tris, 500 mM NaCl, 1 M imidazole, pH 8.0).

The eluted material was dialyzed at 4° C. against Hank's balanced salt solution (HBSS) using MWCO=3500 dialysis tubing. Analysis of the eluted material was performed by polyacrylamide gel electrophoresis from multiple batches and staining with Coomassie blue.

ELISA screen for anti-porcine E-selectin antibodies: To test antibodies for reactivity with porcine E-selectin, an ELISA was carried out using the following protocol:

A 50 μL aliquot of a solution of soluble porcine E-selectin in sodium carbonate/bicarbonate buffer, pH 9.5, was incubated overnight at 4° C. in each test well of a 96 well plate (Nunc-Immuno F96 Polysorp, A/S Nunc, Roskilde, Denmark) in order to bind the protein to the plastic plate. The wells were then subjected to a wash step. (Each wash step consisted of three washes with TBST.) Next, test wells were blocked with 200 μL of blocking solution, 1% BSA in TBS (BSA/TBS), for 1 hour at 37° C. (or, in some cases, 4° C. overnight). After an additional wash step, a 50 μL aliquot of test antibody solution (e.g., hybridoma supernatant) was incubated in each test well for 1 hour at 37° C. with a subsequent wash step.

As a secondary (detection) antibody, 50 μL of a 1:2000 dilution of horseradish peroxidase (HRP) conjugated goat anti-mouse IgG in BSA/TBS was incubated in each test well for 1 hour at 37° C., followed by a wash step. Following the manufacturer's procedures, 10 mg of O-phenylenediamine (Sigma Chemical Company, St. Louis, Mo., Catalog No. P-8287) was dissolved in 25 mLs of phosphate-citrate buffer (Sigma Chemical Company, St. Louis, Mo., Catalog No. P-4922), and 50 μL of this substrate solution was added to each well to allow detection of peroxidase activity. Finally, to stop the peroxidase detection reaction, a 50 μL aliquot of 3N hydrochloric acid was added to each well. The presence of antibodies reactive with porcine E-selectin in the test antibody solutions was read out by a spectrophotometric OD determination at 490 nm.

The solution of soluble porcine E-selectin in sodium carbonate/bicarbonate buffer that served as a source of the protein bound to the plastic plate was used at 2-fold serial dilutions across the plate starting at 50 μg of porcine E-selectin per mL, i.e., at 50, 25, 12.5, 6.25, 3.125, 1.5625, and 0.78125 μg/mL. These dilutions were used to determine the minimum amount of soluble porcine E-selectin that would give maximum sensitivity in this assay. This amount was determined to be the 1.5625 μg/mL dilution.

Northern blot analysis of E-selectin expression in porcine endothelial cells: PAEC were grown to confluence and incubated with D10 supplemented with human IL-1 (20 ng/ml) or TNFα (20 ng/ml) for 4 hr at 37° C. Total RNA was isolated from the cytokine induced and uninduced PAEC as described above. Twenty micrograms from each RNA source was denatured in glyoxal, loaded on a 2% agarose gel in 10 mM phosphate and electrophoresed for 5 hr at 75 volts. RNA was transferred to nitrocellulose (Schleicher and Schuell, Kenne N.H.) by capillary action in 20× SSC. The membrane was prehybridized in BSA/SDS buffer for 2 hr at 650C and subsequently hybridized overnight at 60° C. in the same buffer with a $^{32}$P-labeled probe containing most of the porcine E-selectin coding region as a 1.6Kbp BamHI fragment of the pAPEX-1/pE-selectin plasmid referred to above (specific activity: 2×10$^9$ CPM /μg of DNA).

The blot was washed as follows: two-15 min washes with 2× SSC00.1% SDS at 23° C., two-15 min washes with 0.5× SSC/0.1% SDS at 60° C. and two-15 min washes with 0.2× SSC/0.1% SDS at 60° C. Finally, the blot was exposed to film with intensifying screens for 8 hr at −80° C. The membrane was subsequently stripped in 0.1× SSC at 65° C. for 1 hr before reprobing with a human α-tubulin probe (ATCC #37795) following the procedures described above for probing with the porcine E-selectin coding region probe.

EXAMPLE 1

Molecular Cloning and Sequence Analysis of Porcine E-Selectin

E-selectin homologues have been cloned and characterized from several species including human, mouse, rabbit, cow, and rat (Bevilacqua, et al., 1989; Weller, et al., 1992;

Larigan, et al., 1992; and Fries, et al., 1993). Alignment of E-selectin amino acid sequences from several of these species reveals several regions of shared amino acid identity. Two degenerate oligonucleotides were designed based on sequence homology within the human and mouse E-selectin lectin-like domains. These oligonucleotides were used to PCR amplify the 150 bp fragment referred to above from PAEC cDNA. Analysis of this fragment revealed a unique sequence that was approximately 80% identical to the lectin domains of human and mouse E-selectins.

This 150 bp fragment was used to probe a human cytokine-stimulated PAEC cDNA library and multiple hybridizing clones were obtained. Sequence analysis of a 3.4 kb putative full-length clone revealed 1.9 kb of 3' untranslated DNA and an open reading frame of 1452 nucleotides encoding 484 amino acids (SEQ ID NO:1). Comparison of the predicted amino acid sequence of the porcine molecule with human E-selectin revealed an overall amino acid identity of 75%, while comparison to human P selectin revealed an identity of 44%.

Based on this information, this clone was designated as porcine E-selectin. Analysis of the porcine E-selectin structural domains also revealed homology to human E-selectin including a short signal peptide followed by lectin-like and EGF domains, complement repeats, a short hydrophobic transmembrane domain and a cytoplasmic tail (FIG. 1). The structure of porcine E-selectin differed from that of human E-selectin in that the porcine protein contained only four complement repeats whereas the human protein contained six such repeats. Based on sequence comparison, this divergence appears to have resulted from a deletion of complement repeats 1 and 4.

EXAMPLE 2

E-Selectin Mediated Binding of Human Cells to PAEC

Figure 2B:
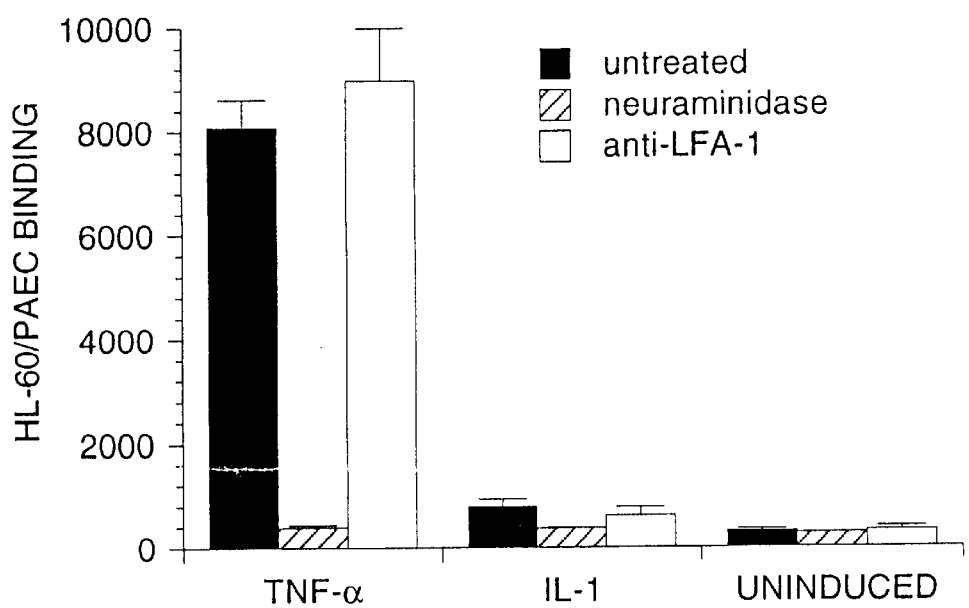

Binding assays were performed between PAEC and human neutrophils or HL-60 cells (FIG. 2). Human neutrophils bound weakly to untreated porcine endothelial cells. However, treatment of PAEC with human TNFα resulted in a marked increase in human neutrophil and HL-60 adhesion (15–20 fold) while induction of PAEC with human IL-1 resulted in only a slight increase in the binding (2 fold) of these cells.

Pre-treatment of human neutrophils and HL-60 cells with neuraminidase completely blocked their adhesion to PAEC, suggesting that sialic acid residues were required for these interactions. Binding assays performed in the presence of a blocking antibody against human LFA-1 failed to inhibit cell adhesion, suggesting that this molecule does not play a significant role in the interactions between PAEC and human neutrophils or HL-60 cells under these assay conditions. Taken together, these data indicate that PAEC express a cytokine inducible cell surface receptor that mediates binding to human neutrophils and HL-60 cells. Further, the requirement for sialic acid, together with the sequence comparisons set forth above in Example 1 and in FIG. 1, indicates that this receptor is functionally and structurally similar to human E-selectin.

EXAMPLE 3

Human Neutrophils and HL-60 Cells Bind to Recombinant E-Selectin Expressed in COS Cells The binding of purified human neutrophils to control transfected, and porcine E-selectin transfected COS cells was analyzed. These experiments were undertaken in order to determine whether porcine E-selectin directly mediates the increased human neutrophil and HL-60 binding to PAEC seen upon stimulation of PAEC with human TNFα and to test whether sialic acid residues on these cells play a critical role in this increased binding.

Figure 3:
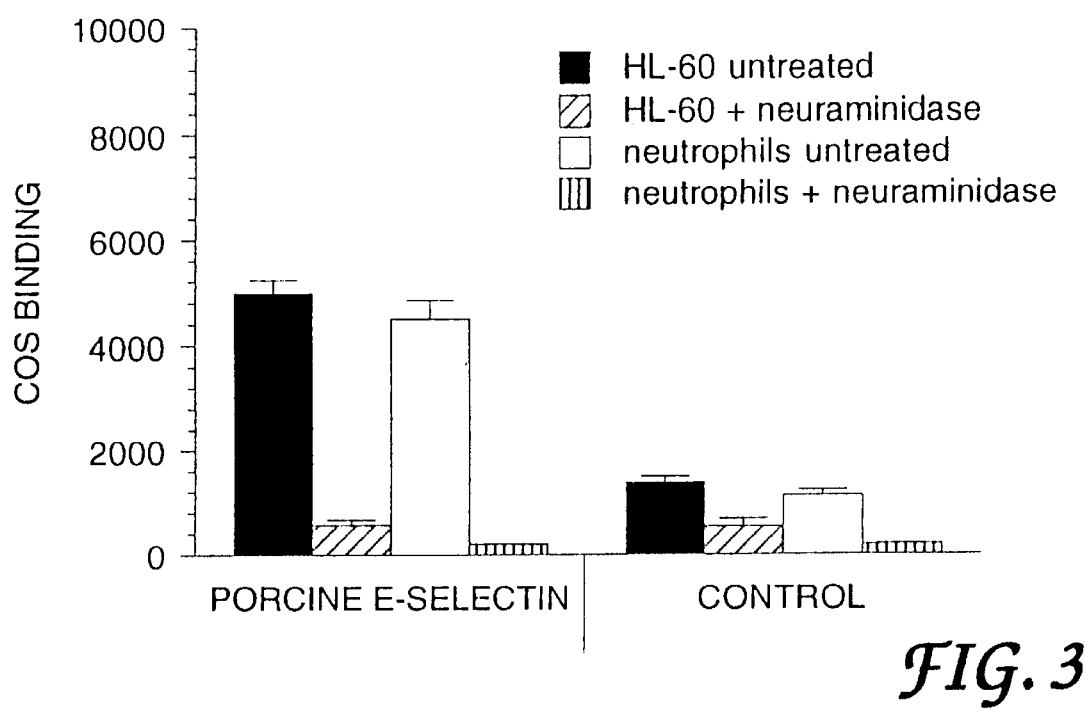
FIG. 3. Binding of human neutrophils and HL-60 cells to COS cells transfected with porcine E-selectin: The binding of calcein-labeled human neutrophils and HL-60 cells to confluent monolayers of either vector control transfected (CONTROL) or porcine E-selectin transfected (PORCINE E-SELECTIN) COS cells was determined. Prior to addition to COS cells, human neutrophils or HL-60 cells were incubated in control buffer or treated with neuraminidase as indicated. Cell binding was determined as described below under the heading "Materials and Methods". Error bars denote standard errors from triplicate determinations from a single experiment and are representative of two so performed.

The results of these studies are presented in FIG. 3. Increased binding (4–5 fold) was observed between human neutrophils or HL-60 cells and COS cells transfected with porcine E-selectin (i.e., pAPEX-1/pE-selectin) as compared to COS cells transfected with vector alone (i.e. the APEX-1 expression vector without the porcine E-selectin encoding insert). As was demonstrated for the binding of human neutrophils and HL-60 to cytokine-induced PAEC, the binding to porcine E-selectin transfected COS cells was completely blocked by prior incubation of human neutrophils with neuraminidase, thereby confirming that sialic acid residues expressed on human leukocytes are required for binding to porcine E-selectin.

Additional binding studies were carried out in the presence of the divalent ion chelating agent EDTA or the relatively calcium ion specific chelating agent EGTA. Since sialic acid mediated binding requires the presence of free calcium ions, inhibition of binding by these chelating agents provides additional evidence for the involvement of sialic acid in these binding interactions.

EXAMPLE 4

Human TNFα Induces Porcine E-Selectin Gene Transcription

Previous studies have shown that human E-selectin gene transcription is induced by the human cytokines TNFα and IL-1, as well as by bacterial lipopolysaccharide (LPS) (Bevilacqua, et al., 1989; and Montgomery, et al., 1991). Induction of E-selectin expression on human endothelial cells occurs within 3–4 hours after cytokine stimulation and returns to background levels after 16–24 hours (Bevilacqua, et al., 1989). As described above, there was a dramatic (15–20 fold) increase in neutrophil binding after stimulation of PAEC with human TNFα but only a minimal increase after stimulation with human IL-1 (FIG. 2). Studies were undertaken to determine if this differential inducibility of PAEC binding correlates with levels of PAEC porcine E-selectin gene transcription.

Northern blots were performed on RNA derived from uninduced PAEC and PAEC induced with either human TNFα or human IL-1 using the full-length porcine E-selectin cDNA as a probe. Hybridization of the porcine E-selectin probe to RNA derived from either unstimulated or human IL-1 stimulated PAEC was not observed. By contrast, the porcine E-selectin probe strongly hybridized to a single RNA species of approximately 3.4 kb derived from human TNFα stimulated PAEC. This band corresponded to the size of the full-length porcine E-selectin cDNA clone isolated from the PAEC library. When probed with the control α-tubulin probe, the same blot showed equivalent levels of hybridization to RNA derived from unstimulated PAEC, human IL-1 stimulated PAEC, or human TNFα stimulated PAEC.

These data parallel the differential effect of human TNFα and IL-1 on human neutrophil/PAEC binding and suggest that porcine E-selectin plays a critical role in the binding of neutrophils to xenograft vascular endothelium in vivo.

EXAMPLE 5

Characterization of Anti-E-Selectin Antibodies

Anti-human-E-selectin monoclonal antibodies were obtained as follows: A commercial anti-human-E-selectin monoclonal antibody ("anti-Elam-1" clone H18/7) was obtained from Collaborative Biomedical Products, Becton Dickenson Labware (Bedford, Mass., Catalog #550023). Anti-human-E-selectin monoclonal antibodies from clones CL-2, CL-3, and CL-37, were obtained from Dr. C. Wayne Smith, Baylor Clinical Care Center, Houston, Tex. (see Mulligan et al. 1991). These antibodies were tested by FACS against PAEC treated with 25ng/ml TNFα, PAEC treated with long/ml IL-1, or untreated PAEC. Only CL-37 bound to the TNFα treated PAEC, and none of the antibodies bound to IL-1 treated or untreated PAEC. CL-37 was also tested and found by FACS analysis to bind to porcine E-selectin expressing COS cells, but not to untransfected COS cells. CL-37 was also shown to bind to soluble porcine E-selectin using the ELISA described above.

EXAMPLE 6

Soluble Porcine E-Selectin

Soluble recombinant porcine E-selectin, prepared as described above, migrated by PAGE as a single Coomassie stained band with an apparent molecular weight of 66 kDa. Since the apparent molecular weight of the soluble porcine E-selectin molecule is higher than would be predicted from its amino acid sequence, it is evident that the molecule is glycosylated.

As discussed in the preceding example, the soluble porcine E-selectin molecule reacted specifically with the anti-human-E-selectin antibody CL-37.

Deposits

Plasmid porcine E-selectin/pBLUESCRIPT SK⁻ was deposited with the American Type Culture Collection, 12301 Parklawn Drive, Rockville, Md., 20852, United States of America, in *E. coli* strain SOLR on May 6, 1994, and has been assigned the designation number ATCC 69616. This deposit was made under the Budapest Treaty on the International Recognition of the Deposit of Microorganisms for the Purposes of Patent Procedure (1977).

Although preferred and other embodiments of the invention have been described herein, a variety of modifications which do not depart from the scope and spirit of the invention will be evident to persons of ordinary skill in the art from this disclosure. The following claims are intended to cover the specific embodiments set forth herein as well as such modifications, variations, and equivalents.

REFERENCES

Allen, et al., 1993. *Circulation* 88, pp. 243.
Ammerer, 1983. *Meth Enzymol* 101, pp. 192.
Auchincloss, 1988. *Transplantation* 46, pp. 1.
Ausubel, et al., 1992. *Current Protocols in Mol Bio*, John Wiley & Sons, New York.
Berg, et al., 1991. *J Biol Chem* 23, pp. 14869.
Bevilacqua and Nelson, 1993. *J Clin Invest* 91, pp. 379.
Bevilacqua, et al., 1989. *Science* 243, pp. 1160.
Bradley, in Robertson (ed), 1987. *Teratocarcinomas and Embryonic Stem Cells a Practical Aoproach*. IRL Press, Eynsham, Oxford, England.
Brinster, et al., 1985. *Proc Natl Acad Sci* 82, pp. 4438–4442.
Brinster, et al., 1989. *Proc Natl Acad Sci* 86, pp. 7087–7091.
Brockmeyer, et al., 1993. *Transplantation* 55, pp. 610.
Capecchi, 1989. *Trends in Genetics* 5(3)pp. 70–76.
Carlos, et al., 1991. *Blood* 77, pp. 2266.
Carson, et al., 1993. *J Rheumatol* 20, pp. 809.
Chang, et al., 1978. *Nature* 275, pp. 615.
Chomczynski and Sacchi, 1987. *Analytical Biology* 162, pp. 156.
Clackson, et al., 1991. *Nature* 352, pp. 624–628.
Cohen, 1989. *Oligodeoxynucleotides, Antisense Inhibitors of Gene Expression*, CRC Press, Inc., Boca Raton, Fla.
Church and Gilbert, 1984. *Proc Natl Acad Sci* 81, pp. 1991.
Coligan, et al., 1992. *Current Protocols in Immunol*, John Wiley & Sons, New York.
Cotran, et al., 1986. *J Exy Med* 164, pp. 661.
Dalmasso, et al., 1992. *Am J Path* 140, pp. 1157.
Davis, et al., 1991. *Science* 253, pp. 59.
Deutscher (ed), 1990. *Guide to Protein Purification, Volume 182*. Academic Press, Inc., San Diego, Calif.
Eguchi, et al., 1991. *Annu Rev Biochem* 60, pp. 631–652.
Evans and Scarpulla, 1989. *Gene* 84, pp. 135.
Ferran, et al., 1993. *Transplantation* 55, pp. 605.
Fries, et al., 1993. *Am Journ Pathol* 143:, pp. 725.
Frohman and Martin, 1989. *Cell* 56, pp. 145–147.
Gearing and Newman, 1993. *Immunol Today* 14(10), pp. 506.
Gearing, et al., 1992. *Annals NY Acad Sci* 667, pp. 324.
Georas, et al., 1992. *Am J Respir Cell Mol Biol* 7, pp. 261.
Goeddel, et al., 1980. *Nucl Acids Res* 8, pp. 4057.
Goeddel (ed), 1990. *Gene Expression Technology, Volume 185*. Academic Press, Inc., San Diego, Calif.
Gossler, et al., 1986. *Proc Natl Acad Sci* 83, pp. 9065–9069.
Graber, et al., 1990. *J Immunol* 145, pp. 819.
Haber, 1992. *Immunol Rev* 130, pp. 189–212.
Hakkert, et al., 1991. *Blood* 78, pp. 2721.
Harlow and Lane, 1988. *Antibodies: A Laboratory Manual*, Cold Spring Harbor Laboratory, Cold Spring Harbor, N.Y.
Harris and Angal (eds), 1989. *Protein Purification Methods: A Practical Approach*. IRL Press, Oxford University Press, Oxford.
Hasty, et al., 1991. *Mol Cell Bio* 11(11), pp. 5586–5591.
Hogan, et al., 1986. *Manipulating the Mouse Embryo: A Laboratory Manual*. Cold Spring Harbor Laboratory, Cold Spring Harbor, N.Y.
Hviid, et al., 1994. *Immunol Letts*. (In press).
Jasin and Berg, 1988. *Genes & Development* 2, pp. 1353–1363.
Jeannotte, et al., 1991. *Mol Cell Bio* 11(11), pp. 557814 5585.
Koch, et al., 1991. *Lab Invest* 64, pp. 313.
Kuijpers, et al., 1991. *J Immunol* 147, pp. 1369.
Larigan, et al., 1992. *DNA Cell Biol* 206, pp. 401.
Lasky, 1992. *Science* 258, pp. 964.
Leeuwenberg, et al., 1992. *Immunology* 77, pp. 543.
Leventhal, et al., 1993. *Transplantation* 55, pp. 857.
Lidell and Cryer, 1991. *A Practical Guide To Monoclonal Antibodies*. John Wiley & Sons, Chichester, West Sussex, England.
Lo, et al., 1991. *J E=Med* 173, pp. 1493.
Lobb, et al., 1991. *J Immunol* 147, pp. 124.
Lovell-Badge, in Robertson (ed), 1987. *Teratocarcinomas and Embryonic Stem Cells a Practical Approach*. IRL Press, Eynsham, Oxford, England.
Luckow, et al., 1988. *Bio/Technology* 6, pp. 47.
Makowka, et al., Sep. 1993. *Second International Congress on Xenotransplantation*, Cambridge, England, abstract 4.
Maniatis, 1982. *Molecular Cloning: A Laboratory Manual*. Cold Spring Harbor Laboratory, Cold Spring Harbor, N.Y., pp. 412.
Mansour, et al., 1988. *Nature* 336, pp. 348–352.
McMahon, et al, 1990. *Cell* 62, pp. 1073–1085.
Mejia-Laguna, et al., 1972. *Am Journ Pathol* 69, pp. 71.
Moir, et al., 1991. *Meth Enzymol* 194, pp. 491–507.
Mollnes, et al., 1988. *Scand J Immunol* 28, pp. 307–312.

Montgomery, et al., 1991. *Proc Natl Acad Sci* 88, pp. 6523.
Montz, et al., 1990. *Cellular Immunol* 127, pp. 337–351.
Morrison, 1992. *Annu Rev Immunol* 10, pp. 239–265.
Mortensen, et al., 1992. *Mol Cell Bio* 12(5), pp. 2391–2395.
Muler-Eberhard, 1988. *Ann Rev Biochem* 57, pp. 321.
Mulligan, et al., 1991. *J Clin Invest* 88, pp. 1396.
Mulligan, et al., 1993. *J Immunol* 151, pp. 6410.
Najarian, 1992. *Transplant Proc* 24, pp. 733.
Newman, et al., 1993. *J Immunol* 150, pp. 633.
Pedersen, et al., 1990. *Transgenic Techniques in Mice—A Video Guide*. Cold Spring Harbor Laboratory, Cold Spring Harbor, N.Y.
Picker, et al., 1991. *Nature* 349, pp. 796.
Pigott, et al., 1992. *Biochem Biophys Res Commun* 187, pp. 584.
Pruitt, et al., 1991. *Transplantation* 52, pp. 868.
Redi, et al., 1991. *Am J Pathol* 139, pp. 461.
Reichmann, et al., 1988. *Nature* 332, pp. 323–327.
*Remington's Pharmaceutical Sciences*. 17th Ed., 1985. Mack Publishing Company, Philadelphia, Pa.
Robertson, et al., 1986. *Nature* 323, pp. 445–448.
Robertson, in Robertson (ed), 1987. *Teratocarcinomas and Embryonic Stem Cells a Practical Approach*. IRL Press, Eynsham, Oxford, England.
Rodrigues, et al., 1993. *J Immunol* 151, pp. 6954–6961.
Sambrook, et al., 1989. *Molecular Cloning: A Laboratory Manual*, 2nd Ed. Cold Spring Harbor Laboratory Press, Cold Spring Harbor, N.Y.
Sanger, et al., 1977. *Proc Natl Acad Sci* 74, pp. 5463.
Satake, et al., Sep. 1993. *Second International Congress on Xenotransplantation*, Cambridge, England, abstract 126.
Schena, et al., 1991. *Meth Enzymol* 194, pp. 389–398.
Shimuzu, et al., 1991. *Nature* 349, pp. 799.
Somervile and d'Apice, 1993. *Kidney Intl* 44, pp. 112.
Taylor, et al., 1992. *Transplantation* 54, pp. 451.
Thomas, et al., 1986. *Cell* 44(3), pp. 419–428.
Thomas, et al., 1987. *Cell* 51(3), pp. 503–512.
Thomas, et al., 1992. *Mol Cell Bio* 12(7), pp. 2919–2923.
Tibell, et al., Sep. 1993. *Second International Congress on Xenotransplantation*, Cambridge, England, abstract 64.
Tuso, et al., 1993. *Transplantation* 55, pp. 1375.
Tyrrell, et al., 1991. *Proc Natl Acad Sci* 88, pp. 10372.
Vercellotti, et al., 1991. *J Immunol* 146, pp. 730.
Weller, et al., 1992. *J Biol Chem* 267, pp. 15176.
Winter and Milstein, 1991. *Nature* 349, pp. 293–299.
Wurzner, et al., 1991. *Complement Inflamm* 8, pp. 328–340.
Zehr, et al., 1994. *Transplantation* 57, pp. 900.

TABLE 1

| BLOOD LEVELS OF CIRCULATING SOLUBLE E-SELECTIN LEVEL IN HEALTHY INDIVIDUALS |
| --- |
| 22 ± 12 ng/ml (n = 62) |
| 0.9 ± 0.7 ng/ml (n = 71) |
| 48 ± 19 ng/ml (n = 64) |
| 16 (range 9–42) ng/ml (n = 89) |
| 22–75 ng/ml (n = 15) |
| FOLD ELEVATION IN DISEASE |
| x 2 Diabetes |
| x 2 Breast/gastro-intestinal cancer |
| x 3–x 9 Septic shock |
| x 23 Septic shock |
| x 4 Systemic lupus erythematosus |
| x 2 Scleroderma |
| x 2 Giant cell arteritis |
| x 2 Polyarteritis nodosa |
| x 2 Malaria |

---

What is claimed is:

1. An isolated porcine E-selectin produced by a method comprising growing a recombinant host cell containing an isolated nucleic acid molecule comprising:
   (a) a nucleic acid molecule encoding amino acid 1 through amino acid 405 of SEQ ID NO:9; or
   (b) a nucleic acid molecule encoding amino acid 1 through amino acid 462 of SEQ ID NO:9, such that the protein encoded by the nucleic acid molecule is expressed by the host cell, and isolating the expressed porcine E-selectin.

2. Isolated porcine E-selectin having the amino acid sequence of SEQ ID NO:9 from amino acid 1 through amino acid 462.

3. Isolated soluble porcine E-selectin comprising the amino acid sequence of SEQ ID NO:9 from amino acid 1 through amino acid 405.

* * * * *